United States Patent
Greco et al.

(10) Patent No.: US 9,878,994 B2
(45) Date of Patent: Jan. 30, 2018

(54) 2-H-INDAZOLE DERIVATIVES AS CYCLIN-DEPENDENT KINASE (CDK) INHIBITORS AND THERAPEUTIC USES THEREOF

(71) Applicant: Beta Pharma, Inc., Wilmington, DE (US)

(72) Inventors: Michael Nicholas Greco, Lansdale, PA (US); Michael John Costanzo, Warminster, PA (US); Jirong Peng, Mequon, WI (US); Victoria Lynn Wilde, Montclair, NJ (US); Don Zhang, Plainsboro, NJ (US)

(73) Assignee: Beta Pharma Inc., Princeton, NJ (US)

( * ) Notice: Subject to any disclaimer, the term of this patent is extended or adjusted under 35 U.S.C. 154(b) by 0 days.

(21) Appl. No.: 15/328,813

(22) PCT Filed: Jul. 24, 2015

(86) PCT No.: PCT/US2015/041915
§ 371 (c)(1),
(2) Date: Jan. 24, 2017

(87) PCT Pub. No.: WO2016/014904
PCT Pub. Date: Jan. 28, 2016

(65) Prior Publication Data
US 2017/0210726 A1   Jul. 27, 2017

Related U.S. Application Data

(60) Provisional application No. 62/028,427, filed on Jul. 24, 2014.

(51) Int. Cl.
*A61K 31/506* (2006.01)
*C07D 401/14* (2006.01)
*A61K 45/06* (2006.01)

(52) U.S. Cl.
CPC .......... *C07D 401/14* (2013.01); *A61K 31/506* (2013.01); *A61K 45/06* (2013.01)

(58) Field of Classification Search
CPC ..................... A61K 31/506; C07D 401/14
See application file for complete search history.

(56) References Cited

U.S. PATENT DOCUMENTS 7,855,211 B2    12/2010  Coates et al.
2010/0076027 A1   3/2010  Benson et al.

FOREIGN PATENT DOCUMENTS

WO    2007124288 A1   11/2007
WO    2009158571 A1   12/2009

OTHER PUBLICATIONS

Genung et al., "Regioselective Synthesis of 2H-Indazoles Using a Mild, One-Pot Condensation-Cadogan Reductive Cyclization," Oranic Letters (2014); 16:3114-3117.
Dubrovskiy et al., "Synthesis of o-(Dimethylamino)aryl Ketones, Acridones, Acridiniium Salts, and 1H-Indazoles by the Reaction of Hydrazones and Arynes," J. Org. Chem. (2012); 77(24):1-55.

*Primary Examiner* — Michael Barker
(74) *Attorney, Agent, or Firm* — Fox Rothchild LLP

(57) ABSTRACT

Indazole compounds of formula (I) as cyclin-dependent kinase (CDK) and cell-proliferation inhibitors, and therapeutic uses and methods of preparation thereof, are disclosed. These compounds, and pharmaceutically acceptable salts, solvates, prodrugs, and pharmaceutical compositions thereof, are useful for treating diseases and disorders associated with activity of cyclin-dependent kinases, in particular CDK4/6, including but not limited to various cancers and inflammation-related diseases or conditions.

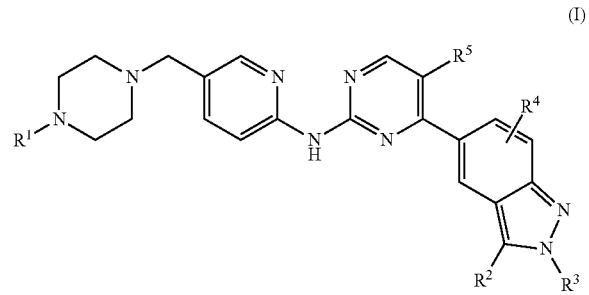

32 Claims, No Drawings

2-H-INDAZOLE DERIVATIVES AS CYCLIN-DEPENDENT KINASE (CDK) INHIBITORS AND THERAPEUTIC USES THEREOF

CROSS REFERENCE TO RELATED APPLICATIONS

This application is the U.S. National Phase of International Application No. PCT/US2015/041915, filed on Jul. 24, 2015, which claims priority under 35 U.S.C. § 119(e) to U.S. Provisional Application No. 62/028,427, filed on Jul. 24, 2014, the disclosures of which are incorporated herein by reference in their entirety.

FIELD OF THE INVENTION

The present invention is related to the field of compounds, compositions and methods for the treatment or prevention of a disease, disorder, or medical condition mediated through certain cyclin-dependent kinases (CDKs). The diseases include various cancers.

BACKGROUND OF THE INVENTION

Cyclin-dependent kinases are a family of protein kinases that regulate cell division and proliferation. Cell cycle progression is controlled by cyclins and their associated cyclin-dependent kinases, such as CDK1, CDK2, CDK3, CDK4 and CDK6, while other CDKs such as CDK7, CDK8 and CDK9 are critical to transcription. CDK binding to cyclins forms heterodimeric complexes that phosphorylate their substrates on serine and threonine residues, which in turn initiates events required for cell-cycle transcription and progression. Since uncontrolled cell proliferation is a hallmark of cancer, and most cancer cells exhibit deregulation of CDKs, inhibition of CDKs has emerged as a potential treatment for various cancers. Inhibitors with varying degrees of selectivity for CDKs have been reported; however, selective CDK4/6 inhibitors are currently viewed as a promising class of potential anticancer or anti-inflammatory agents due to both the critical role of CDK4/6 in regulating cell proliferation and the toxic effects associated with inhibition of other members of the CDK family.

Recently, several types of aminopyrimidine derivatives have been reported to be selective CDK4/6 inhibitors. See, e.g., WO 2003/062236, WO 2007/140222, and US 2010/0160340. Each of these types of molecules contains a 2-aminopyrimidine moiety bound through the 2-amino group to an aryl or heteroaryl ring system. There remains a need to develop new CDK 4/6 inhibitors as novel anticancer and/or anti-inflammatory agents.

SUMMARY OF THE INVENTION

The present invention relates to 2-aminopyrimidine-substituted indazole derivatives that are effective as selective CDK inhibitors and useful in the treatment or prevention of diseases, disorders, or medical conditions mediated through certain CDKs, in particular CDK4 and CDK6, such as various types of cancers and inflammation-related conditions.

One aspect of the present invention is directed to a compound of formula (I):

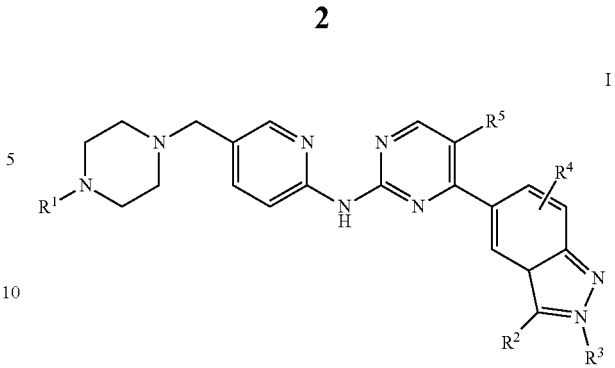

or a pharmaceutically acceptable salt, solvate, or prodrug thereof, wherein:

$R^1$ is selected from the group consisting of hydrogen, linear or branched $C_1$-$C_8$ alkyl, and $C_3$-$C_7$ cycloalkyl;

$R^2$ and $R^3$ are independently selected from the group consisting of hydrogen, linear or branched $C_1$-$C_8$ alkyl, $C_3$-$C_7$ cycloalkyl, and cycloalkylmethyl;

$R^4$ is selected from the group consisting of hydrogen, halogen, linear or branched $C_1$-$C_8$ alkyl, and $C_3$-$C_7$ cycloalkyl; and $R^5$ is hydrogen or halogen.

Another aspect of the present invention is directed to a pharmaceutical composition comprising a compound of formula (I), or a pharmaceutically acceptable salt, solvate, or prodrug thereof, and one or more pharmaceutically acceptable excipients, such as adjuvants, diluents, and/or carriers.

Another aspect of the present invention is directed to a method of treating a disease, disorder, or condition mediated through at least one of cyclin-dependent kinases (CDK), in particular CDK4, CDK6, or a combination thereof, comprising administering to a subject in need thereof a therapeutically effective amount of a compound of formula (I), or a pharmaceutically acceptable salt, solvate, or prodrug thereof.

Another aspect of the present invention is directed to a method of treating a disease, disorder, or condition mediated through at least one of cyclin-dependent kinases (CDK), in particular CDK4, CDK6, or a combination thereof, comprising administering to a subject in need thereof a therapeutically effective amount of a pharmaceutical composition comprising a compound of formula (I), or a pharmaceutically acceptable salt, solvate, or prodrug thereof, and one or more pharmaceutically acceptable excipients, such as adjuvants, diluents, and/or carriers.

In one embodiment, the diseases, disorders, or conditions associated with one or more cyclin-dependent kinases, in particular CDK4, CDK6, or a combination thereof, comprise cancers, which may include, but are not limited to, lung cancer, especially non-small cell lung cancer (NSCLC), breast cancer, prostate cancer, colorectal cancer, glioblastoma, mantel cell lymphoma, chronic myeloid leukemia and acute myeloid leukemia, and complications thereof. In another embodiment, the diseases, disorders, or conditions comprise the inflammation-related diseases and conditions, such as arthritis, e.g., rheumatic arthritis, and cystic fibrosis.

Another aspect of the invention is directed to a method of inhibiting cell proliferation comprising treating the cells with an effective amount of a compound of formula (I), or a salt, solvate, prodrug, or composition thereof.

Another aspect of the invention is directed to a method of inhibiting a cyclin-dependent kinase (CDK), in particular CDK4, CDK6, or a combination thereof, comprising treating the kinase with an effective amount of a compound of formula (I), or a salt, solvate, prodrug, or composition thereof.

Another aspect of the present invention is directed to use of the compounds of this invention for the study of CDKs in biological and pathological phenomena and for comparative evaluation of new kinase inhibitors.

Another aspect of the present invention is directed to use of a compound of formula (I) according to any embodiments described herein, or a pharmaceutically acceptable salt, solvate, prodrug, or composition thereof, in the manufacture of a medicament for treatment of a disease or disorder associated with a CDK activity. The CDK activity is preferably activity of CDK4, CDK6, or a combination thereof.

Still another aspect of the present invention is directed to the methods of synthesizing the compounds of formula (I) as substantially disclosed and described herein.

Other aspects or advantages of the present invention will be apparent to those skilled in the art in view of the following detailed description and claims in combination with the knowledge and skills generally known in the field.

DETAILED DESCRIPTION OF THE INVENTION

The present invention provides novel 2-aminopyrimidine-substituted 2H-indazole derivatives useful as CDK inhibitors.

In one aspect, the present invention provides a compound of formula (I):

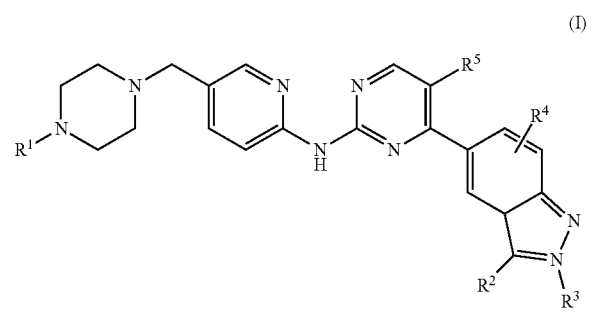

(I)

or a pharmaceutically acceptable salt, solvate, or prodrug thereof, wherein:

$R^1$ is selected from the group consisting of hydrogen, $C_1$-$C_8$ alkyl, and $C_3$-$C_7$ cycloalkyl;

$R^2$ and $R^3$ are independently selected from the group consisting of hydrogen, linear or branched $C_1$-$C_8$ alkyl, $C_3$-$C_7$ cycloalkyl, and $C_3$-$C_7$ cycloalkylmethyl;

$R^4$ is selected from the group consisting of hydrogen, halogen, linear or branched $C_1$-$C_8$ alkyl, and $C_3$-$C_7$ cycloalkyl; and $R^5$ is hydrogen or halogen.

In one embodiment of this aspect, $R^1$ is $C_1$-$C_6$ alkyl.

In another embodiment of this aspect, $R^1$ is methyl, ethyl, propyl, or isopropyl.

In another embodiment of this aspect, $R^2$ is $C_1$-$C_6$ alkyl, $C_3$-$C_6$ cycloalkyl, or $C_3$-$C_6$ cycloalkylmethyl.

In another embodiment of this aspect, $R^2$ is methyl, ethyl, propyl, isopropyl, cyclopropyl, cyclopentyl, cyclopropylmethyl, or cyclopentylmethyl.

In another embodiment of this aspect, $R^3$ is $C_1$-$C_6$ alkyl or $C_3$-$C_6$ cycloalkyl.

In another embodiment of this aspect, $R^3$ is methyl, ethyl, propyl, isopropyl, or cyclopropyl.

In certain embodiments, the present invention provides a compound of formula (I), wherein the $R^4$ substituent is attached at the 7-position of the indazole moiety, as in formula (Ia):

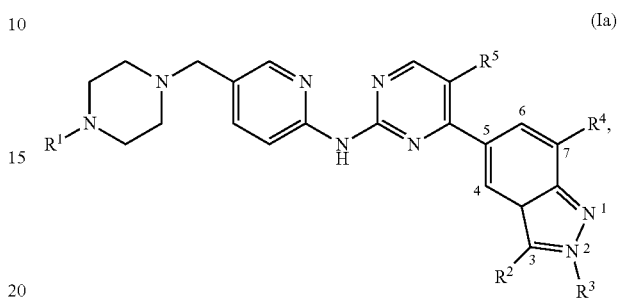

(Ia)

or a pharmaceutically acceptable salt, solvate, or prodrug thereof, wherein:

$R^1$ is selected from the group consisting of hydrogen, $C_1$-$C_8$ alkyl, and $C_3$-$C_7$ cycloalkyl;

$R^2$ and $R^3$ are independently selected from the group consisting of hydrogen, $C_1$-$C_8$ alkyl, $C_3$-$C_7$ cycloalkyl, and cycloalkylmethyl;

$R^4$ is selected from the group consisting of hydrogen, halogen, $C_1$-$C_8$ alkyl, and $C_3$-$C_7$ cycloalkyl; and $R^5$ is hydrogen or halogen.

In another embodiment of this aspect, $R^4$ is hydrogen or halogen.

In another embodiment of this aspect, $R^5$ is hydrogen or fluoride.

In another embodiment of this aspect, $R^1$ is methyl or ethyl; $R^2$ is isopropyl, cyclopropyl, cyclopropylmethyl, or cyclopentyl; $R^3$ is methyl or ethyl, $R^4$ is hydrogen or fluoro, and $R^5$ is hydrogen or fluoro.

In certain preferred embodiments of this aspect, the $R^4$ substituent is attached at the 7-position of the indazole moiety, and $R^5$ is fluorine, characterized by formula (Ib):

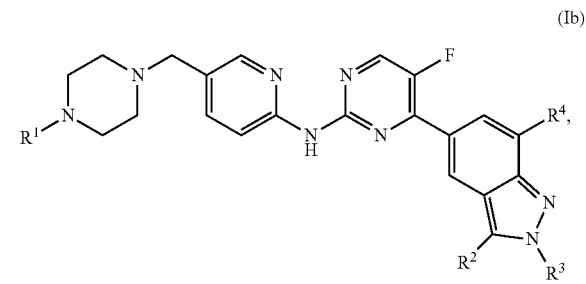

(Ib)

wherein $R^4$ is preferably hydrogen or halogen; and when $R^4$ is a halogen, it is preferably chlorine or fluorine, more preferably fluorine.

In certain preferred embodiments of this aspect, the present invention provides a compound of formula selected from the group consisting of:

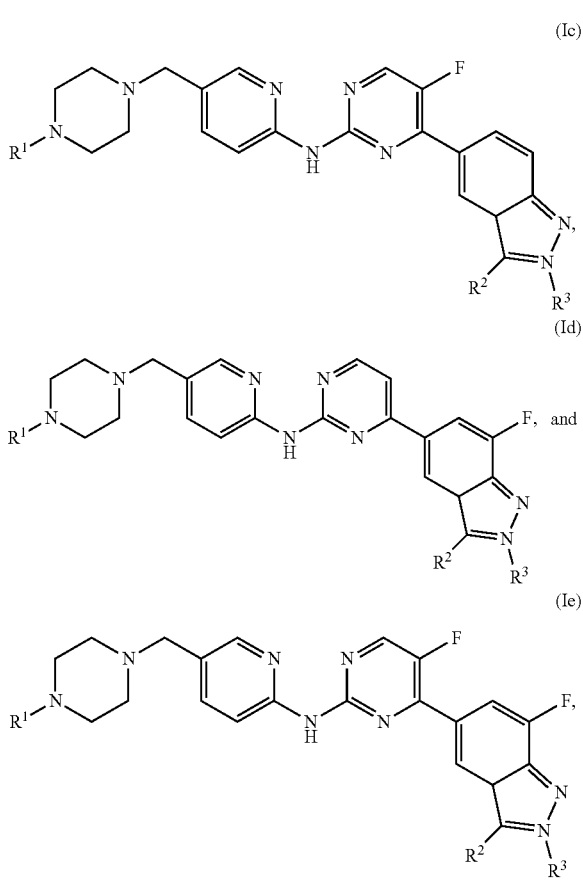

or a pharmaceutically acceptable salt, solvate, or prodrug thereof, wherein $R^1$, $R^2$, and $R^3$ are each defined in any of the embodiments described here.

In certain preferred embodiments of this aspect, the present invention provides the compounds listed in Table 1 (infra), and pharmaceutically acceptable salts, solvates, and prodrugs thereof.

In another aspect, the present invention provides a pharmaceutical composition comprising a compound of formula (I), (Ia), (Ib), (Ic), (Id), or (Ie) according to any embodiments described here, or a pharmaceutically acceptable salt, solvate, or prodrug thereof, and one or more pharmaceutically acceptable adjuvants, diluents, and/or carriers.

In another aspect, the present invention provides a method of treating a disease, disorder, or condition mediated through activity of at least one cyclin-dependent kinase (CDK), comprising administering to a subject in need thereof a therapeutically effective amount of the compound of formula (I), (Ia), (Ib), (Ic), (Id), or (Ie) according to any of the embodiments described herein, or a pharmaceutically acceptable salt, solvate, or prodrug thereof.

In one embodiment of this aspect, the present invention provides a method of treating a disease, disorder, or condition mediated through activity of at least one cyclin-dependent kinase (CDK), comprising administering to a subject in need thereof a pharmaceutical composition comprising a therapeutically effective amount of the compound of formula (I), (Ia), (Ib), (Ic), (Id), or (Ie) according to any of the embodiments described herein, or a pharmaceutically acceptable salt, solvate, or prodrug thereof, and one or more pharmaceutically acceptable adjuvants, diluents, and/or carriers.

In one preferred embodiment of this aspect, the at least one CDK is CDK4, CDK6, or a combination thereof.

In another preferred embodiment of this aspect, the disease or disorder is a cancer or an inflammation-related disease or condition.

In another preferred embodiment of this aspect, the inflammation-related disease or condition is arthritis, such as rheumatic arthritis, or cystic fibrosis.

In another preferred embodiment of this aspect, the cancer is selected from, but not limited to, colorectal cancer, breast cancer, lung cancer, especially non-small cell lung cancer (NSCLC), prostate cancer, glioblastoma, mantel cell lymphoma (MCL), chronic myeloid leukemia (CML), acute myeloid leukemia (AML), and complications thereof.

In another embodiment of this aspect, the compound of the present invention may be administered to a subject in need thereof in combination with administration of a second therapeutic agent.

In another embodiment, the second therapeutic agent is a different CDK inhibitor, a human epidermal growth factor receptor (e.g., HER2) inhibitor, a serine/threonine kinase inhibitor, such as a mammalian target of rapamycin (mTOR) inhibitor, or an epidermal growth factor receptor (EGFR) inhibitor.

In another aspect, the present invention provides a method of inhibiting cell proliferation, comprising treating the cells with an effective amount of the compound of formula (I) according to any of the embodiments described, or a salt, solvate, prodrug, or composition thereof. The method of inhibiting cell proliferation can take place in vivo, e.g., inside the body of a subject, or in vitro, e.g., in a biological sample containing the proliferative cells of a subject.

In a preferred embodiment of this aspect, the proliferative cells are cancer cells, such as, but not limited to, cells of colorectal cancer, breast cancer, lung cancer, especially non-small cell lung cancer (NSCLC), prostate cancer, glioblastoma, mantel cell lymphoma (MCL), chronic myeloid leukemia (CML), acute myeloid leukemia (AML), or complications thereof.

In another aspect, the present invention provides a method of inhibiting a cyclin-dependent kinase (CDK) comprising treating said kinase with an effective amount of a compound of formula (I) according to any embodiments described herein, or a salt, solvate, prodrug, or composition thereof. The method of inhibiting CDK can take place in vivo, e.g., inside the body of a subject, or in vitro, e.g., in a biological sample containing the proliferative cells of a subject.

In a preferred embodiment of this aspect, the cyclin-dependent kinase is CDK4, CDK6, or a combination thereof.

In another aspect, the present invention provides use of a compound of formula (I), (Ia), (Ib), (Ic), (Id), or (Ie) according to any embodiments described herein, or a pharmaceutically acceptable salt, solvate, prodrug, or composition thereof, in the manufacture of a medicament for treatment of a disease or disorder associated with a CDK activity. The CDK activity is preferably activity of CDK4, CDK6, or a combination thereof.

In one embodiment of this aspect, the disease or disorder is selected from the group consisting of colorectal cancer, breast cancer, lung cancer, especially non-small cell lung cancer (NSCLC), prostate cancer, glioblastoma, mantel cell lymphoma (MCL), chronic myeloid leukemia (CML), and acute myeloid leukemia (AML).

In another embodiment of this aspect, the disease or disorder is an inflammation-related disease or condition, such as arthritis, in particular rheumatic arthritis, or cystic fibrosis.

In another aspect, the present invention provides a method of preparing a compound of formula (I), comprising a step of coupling intermediate E with intermediate G:

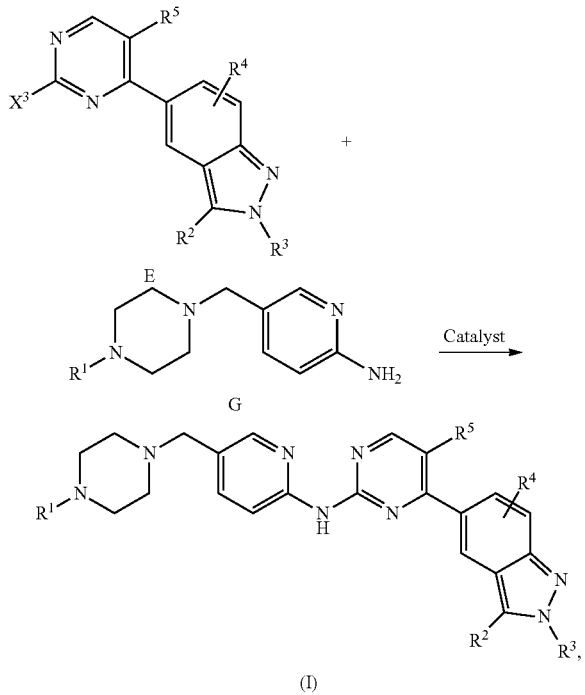

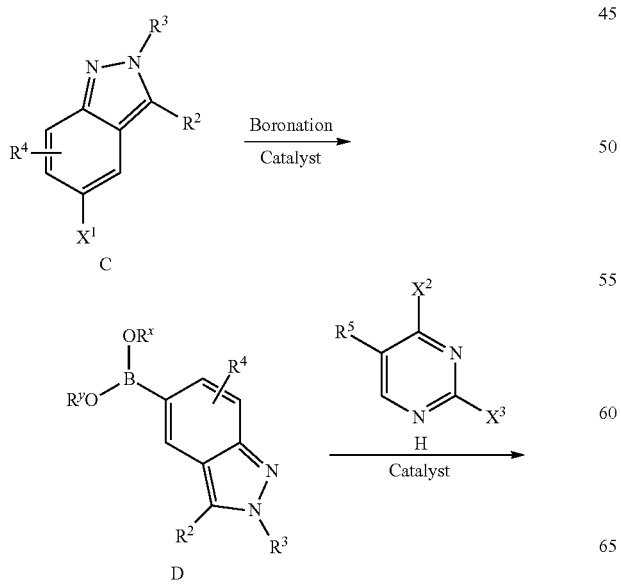

wherein $R^1$ through $R^5$ are defined according to any of the embodiments described herein, and $X^3$ is Cl, Br, or I.

In one embodiment of this aspect, the method further includes the steps of converting intermediate C to intermediate D and coupling the intermediate D with a pyrimidine compound H to form the intermediate E:

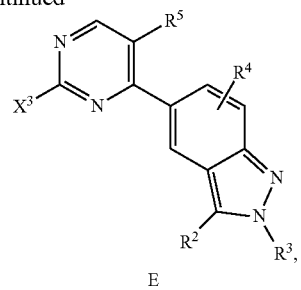

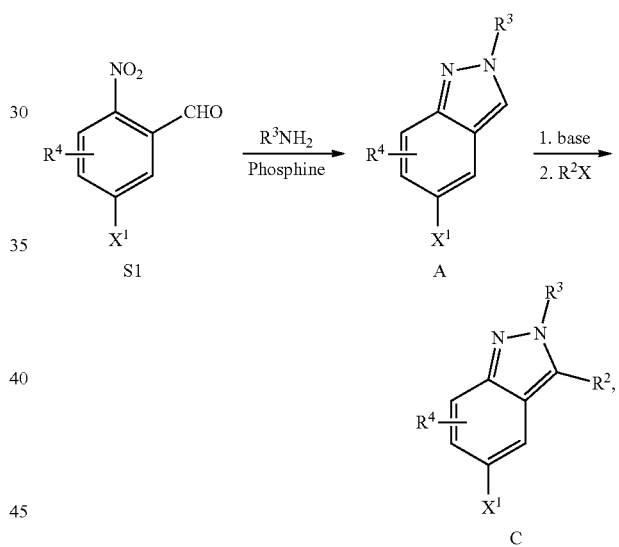

wherein $R^x$ and $R^y$ are independent alkyl, aryl, cycloalkyl, or alternatively together form an alkylene group, each optionally substituted by one or more substituents independently selected from $C_1$-$C_4$ alkyl, halogen or phenyl; and wherein $X^1$, $X^2$, and $X^3$ are each independently Cl, Br, or I, on condition that the intermediate D couples with the compound H selectively at the $X^2$ site over the $X^3$ site, preferably having a higher than 90:10 selectivity, more preferably having a 95:5 selectivity, and most preferably exclusively at the $X^2$ site.

In one embodiment of this aspect, the method further includes the steps of converting starting material S1 to intermediate A and converting the intermediate A to the intermediate C:

wherein $X^1$ is Cl, Br, I, or MeSO$_3$—; and wherein $R^2$ and $R^3$ are as defined according to any of the embodiments described herein.

In another embodiment of this aspect, the method further includes converting the intermediate A to the intermediate C, alternatively, comprises converting the intermediate A to an alcohol intermediate B followed by reduction of the alcohol intermediate B to form the intermediate C:

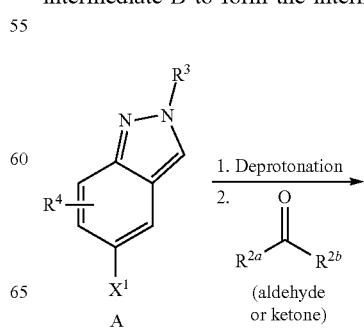

-continued

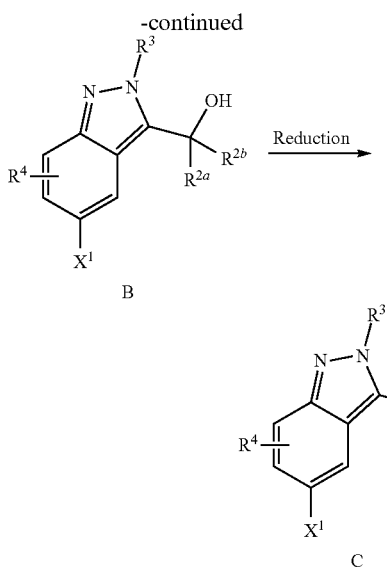

B

C wherein $R^{2a}$ and $R^{2b}$ are each independently hydrogen, alkyl, cycloalkyl, or together form an alkylene group so that the group

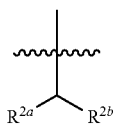

formed in the intermediate C is $R^2$ as defined according to any of the embodiments described herein.

In one embodiment of this aspect, the method further includes a step of forming the intermediate G through coupling the pyridine aldehyde compound S2 and the piperazine compound S3 to form an intermediate F, followed by converting the intermediate F to the intermediate G:

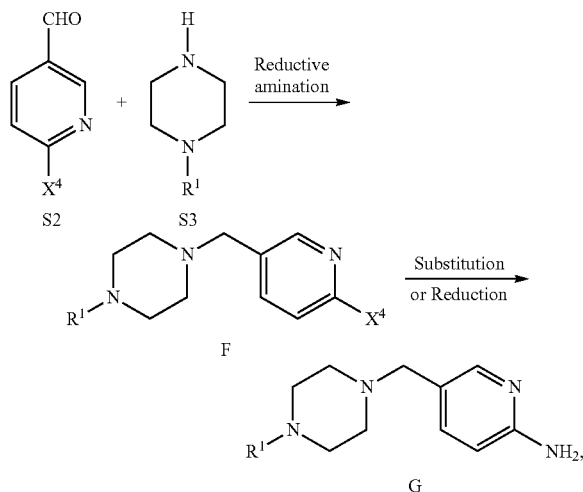

wherein $X^4$ is selected from the group consisting of Cl, Br, I, and —$NO_2$; and wherein said converting the intermediate F to the intermediate G comprises replacing $X^4$ with $NH_2$ when $X^4$ is Cl, Br, or I; or alternatively reducing the nitro group (—$NO_2$) to amino group (—$NH_2$) when $X^4$ is —$NO_2$.

Compounds provided by this invention are also useful for the study of kinases in biological and pathological phenomena, the study of transduction pathways mediated by such kinases, and the comparative evaluation of new kinase inhibitors.

Unless otherwise indicated, the term "alkyl," as used herein, is intended to include both branched and straight-chain saturated aliphatic hydrocarbon groups containing 1 to 8 carbons, preferably 1 to 6, more preferably 1 to 4, carbons. The term encompasses, but is not limited to, methyl, ethyl, propyl, isopropyl, butyl, t-butyl, isobutyl, pentyl, hexyl, or the like.

Unless otherwise indicated, the term "alkylene," as used herein, refers to a bivalent saturated aliphatic radical derived from an alkane by removal of two hydrogen atoms. Examples include, but are not limited to, methylene (—$CH_2$—), ethylene (—$CH_2CH_2$—), propylene (—$CH_2CH_2CH_2$—), or the like.

Unless otherwise indicated, the term "cycloalkyl", as used herein alone or as a part of another group, includes saturated cyclic hydrocarbon radical having 3 to 8 carbons forming the ring. Examples include, but are not limited to, cyclopropyl, cyclobutyl, cyclopentyl, and cyclohexyl.

Unless otherwise indicated, the term "aryl", as used herein alone or as part of another group, refers to monocyclic or bicyclic aromatic radical containing 6 to 10 carbons in the ring portion (such as phenyl and naphthyl, including 1-naphthyl and 2-naphthyl).

"Halo" or "halogen" as used herein, refers to fluoro (F), chloro (Cl), bromo (Br), and iodo (I).

Further, the alkyl, alkylene, cycloalkyl, and cycloalkyl-methyl groups optionally can be independently further substituted with one or more, preferably 1 to 3, substituents independently selected from the group consisting of halogen and $C_1$-$C_4$ alkyl.

The compounds of the present invention are generally recognized as organic bases, which are able to react with acids, specifically pharmaceutically acceptable acids, to form pharmaceutically acceptable salts.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. See, e.g., S. M. Berge et al., *J. Pharm. Sci.*, 1977, 66, 1-19, which is incorporated herein by reference. Pharmaceutically acceptable salts of the compounds of this invention include those derived from suitable inorganic and organic acids. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Preferred pharmaceutically acceptable salts include the hydrochloride salts.

The term "solvate," as used herein, means a physical association of a compound of this invention with a stoichiometric or non-stoichiometric amount of solvent molecules. For example, one molecule of the compound associates with one or more, preferably one to three, solvent molecules. It is also possible that multiple (e.g., 1.5 or 2) molecules of the compound share one solvent molecule. This physical association may include hydrogen bonding. In certain instances the solvates will be capable of isolation as crystalline solid. The solvent molecules in the solvate may be present in a regular arrangement and/or a non-ordered arrangement. Exemplary solvates include, but are not limited to, hydrates, ethanolates, methanolates, and isopropanolates. Methods of solvation are generally known in the art.

The term "prodrug," as used herein, refers to a derivative of a compound that can be transformed in vivo to yield the parent compound, for example, by hydrolysis in blood. Common examples of prodrugs in the present invention include, but are not limited to, amide or phosphoramide forms of an active amine compound, for example, the compound of formula (II):

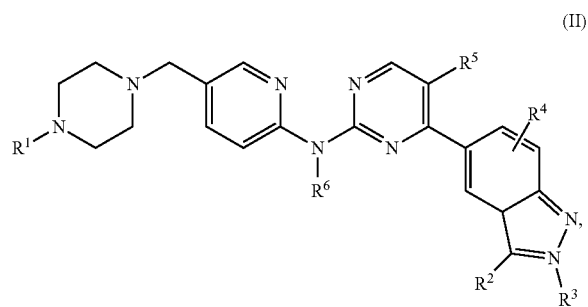

(II)

wherein $R^6$ is an acyl group (e.g., acetyl, propionyl, formyl, etc.) or phosphoryl [e.g., —P(=O)(OH)$_2$] group; or alternatively, when $R^1$ or $R^3$ in an active compound is hydrogen, the corresponding amide or phosphoramide compounds may serve as prodrugs. Such amide or phosphoramide prodrug compounds may be prepared according to conventional methods as known in the art.

When it is possible that, for use in therapy, therapeutically effective amounts of a compound of the present invention, or pharmaceutically acceptable salts or solvates thereof, may be administered as the raw chemical, it is possible to present the active ingredient as a pharmaceutical composition. Accordingly, the disclosure further provides pharmaceutical compositions, which include any compounds of the present invention, or pharmaceutically acceptable salts or solvates thereof, and one or more, preferably one to three, pharmaceutically acceptable carriers, diluents, or other excipients. The carrier(s), diluent(s), or other excipient(s) must be acceptable in the sense of being compatible with the other ingredients of the formulation and not deleterious to the subject being treated.

The term "pharmaceutically acceptable," as used herein, refers to the property of those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Typically, the pharmaceutical compositions of this disclosure will be administered from once every 1 to 5 days to about 1-5 times per day, or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford effective results without causing substantial harmful or deleterious side effects.

When the compositions of this disclosure comprise a combination of a compound of the present disclosure and one or more, preferably one or two, additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example, by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation.

A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release, for example, by coating or embedding particulate material in polymers, wax, or the like.

It should be understood that in addition to the ingredients particularly mentioned above, the formulations may include other agents conventional in the art having regard to the type of formulation in question, for example those suitable for oral administration may include flavoring agents.

The term "subject" or "patient" includes both humans and other mammalian animals, preferably humans.

The term "therapeutically effective amount" refers to an amount of a compound or composition that, when administered to a subject for treating a disease, is sufficient to effect such treatment for the disease. A "therapeutically effective amount" can vary depending on, inter alia, the compound, the disease and its severity, and the age, weight, or other factors of the subject to be treated. When applied to an individual active ingredient, administered alone, the term refers to that ingredient alone. When applied to a combination, the term refers to combined amounts of the active ingredients that result in the therapeutic effect, whether administered in combination, serially, or simultaneously.

In some embodiments, the term "treating" or "treatment" refers to: (i) inhibiting the disease, disorder, or condition, i.e., arresting its development; (ii) relieving the disease, disorder, or condition, i.e., causing regression of the disease, disorder, and/or condition; or (iii) preventing a disease, disorder or condition from occurring in a subject that may be predisposed to the disease, disorder, and/or condition but has not yet been diagnosed as having it. Thus, in some embodiments, "treating" or "treatment" refers to ameliorating a disease or disorder, which may include ameliorating one or more physical parameters, though maybe indiscernible by the subject being treated. In some embodiments, "treating" or "treatment" includes modulating the disease or disorder, either physically (e.g., stabilization of a discernible symptom) or physiologically (e.g., stabilization of a physical parameter) or both. In yet some embodiments, "treating" or "treatment" includes delaying the onset of the disease or disorder.

Methods

Abbreviations

The following abbreviations may be used in this application:

$B_2pin_2$=bis(pinacolato)diboron
MeOH=methanol
LDA=lithium diisopropylamide
LiHMDS=lithium bis(trimethylsilyl)amide [LiN(SiMe3)2]
Pd(dppf)Cl$_2$=[1,1'-bis(diphenylphosphino)ferrocene]dichloropalladium(II)
Pd$_2$(dba)$_3$=tris(dibenzylideneacetone)dipalladium(0)
Xantphos=4,5-bis(diphenylphosphino)-9,9-dimethylxanthene
nBu$_3$P=tri-n-butylphosphine
DCM=dichloromethane
THF=tetrahydrofuran;
DIEA=DIPEA=diisopropylethylamine;
sat.=saturated aqueous solution;
aq.=aqueous
FCC=flash column chromatography using silica;
TFA=trifluoroacetic acid;
r.t.=room temperature;
DMF=N,N-dimethylformamide;
DMSO=dimethylsulfoxide;
DMA=N,N-dimethylacetamide;
EtOAc=ethyl acetate;
h=hour(s).

CHEMICAL SYNTHESIS

Synthesis of Compounds of Formula (I)

The synthesis of compounds of formula (I) is exemplified in the General Synthetic Schemes 1-4:

1. Synthesis of the Indazole Intermediate C
(Scheme 1)

A suitable 5-halo-2-nitrobenzaldehyde starting material S1 ($X^1$=Cl, Br, or I) is allowed to react with a primary amine ($R^3NH_2$) in the presence of a phosphine, e.g., tributylphosphine, to form the indazole derivative A (Genung, N. E. et al. *Org. Lett.* 2014 16, 3114-3117), which in turn is deprotonated at the 3-position using a strong base, e.g., LDA, followed by reaction with an alkylation reagent $R^2X$ (X=e.g., Cl, Br, I, or methanesulfonate) to form the intermediate C with the desired $R^2$, $R^3$, and $R^4$ in place. Alternatively, the deprotonated compound A can be allowed to react with an aldehyde or ketone to form an alcohol adduct, which is reduced (e.g., by a dialkylsilane) to form the desired intermediate C.

2. Synthesis of the Pyrimidine-Substituted Indazole Intermediate E (Scheme 2)

The intermediate C is allowed to undergo a boronation reaction in the presence of a catalyst (e.g., a palladium catalyst) to form the boronate intermediate D, which is allowed to couple with a halogen-substituted pyrimidine derivative H to form a 5-(pyrimidin-3-yl)-indazole intermediate E.

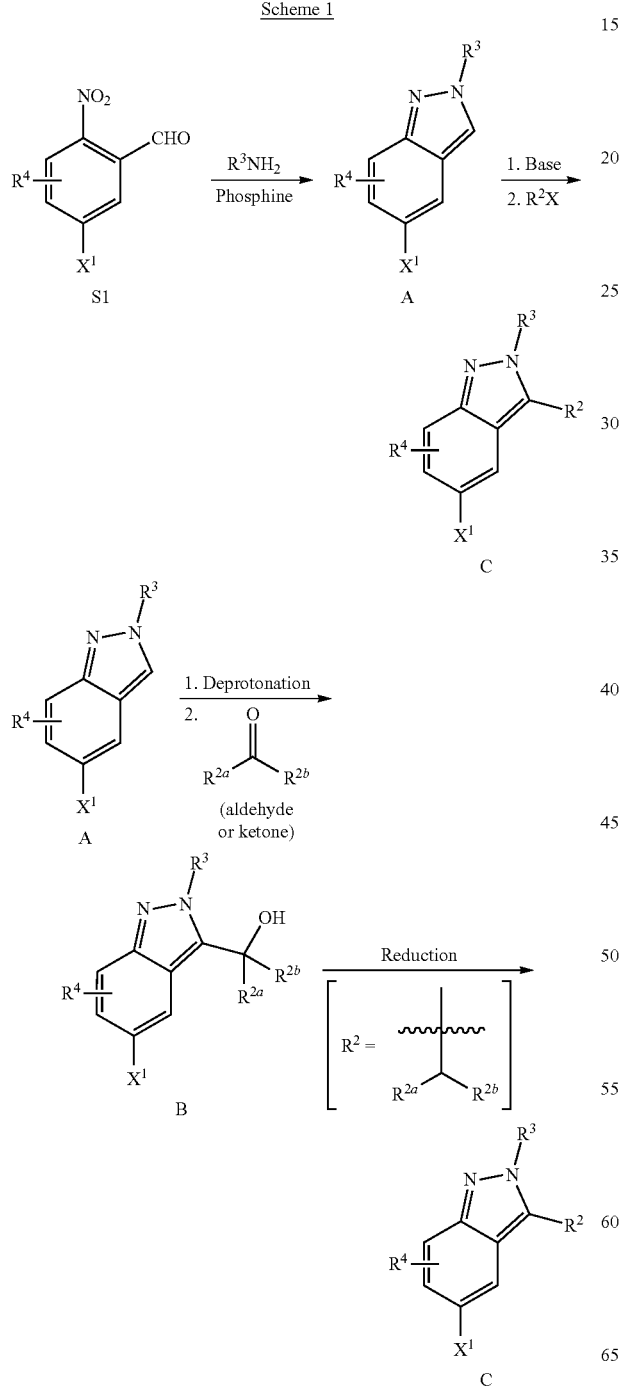

Scheme 1

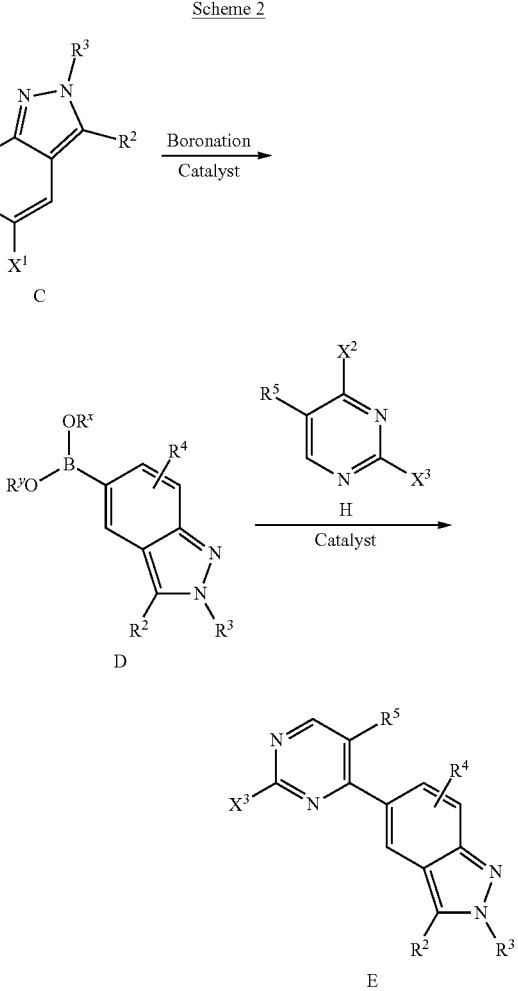

Scheme 2

3. Synthesis of the 2-amino-5-piperazinylmethyl-pyridine Intermediate G (Scheme 3)

A 6-halogen or 6-nitro substituted pyridine-3-carbaldehyde starting material S2 and a 1-$R^1$-substituted piperazine starting material S3 are allowed to undergo a reductive amination reaction to form a 2-amino-5-piperazinylmethyl-pyridine intermediate F, which is in turn converted to the 2-amino-5-piperazinylmethyl-pyridine intermediate G through substitution of the halogen or reduction of nitro group on the pyridine ring.

Scheme 3

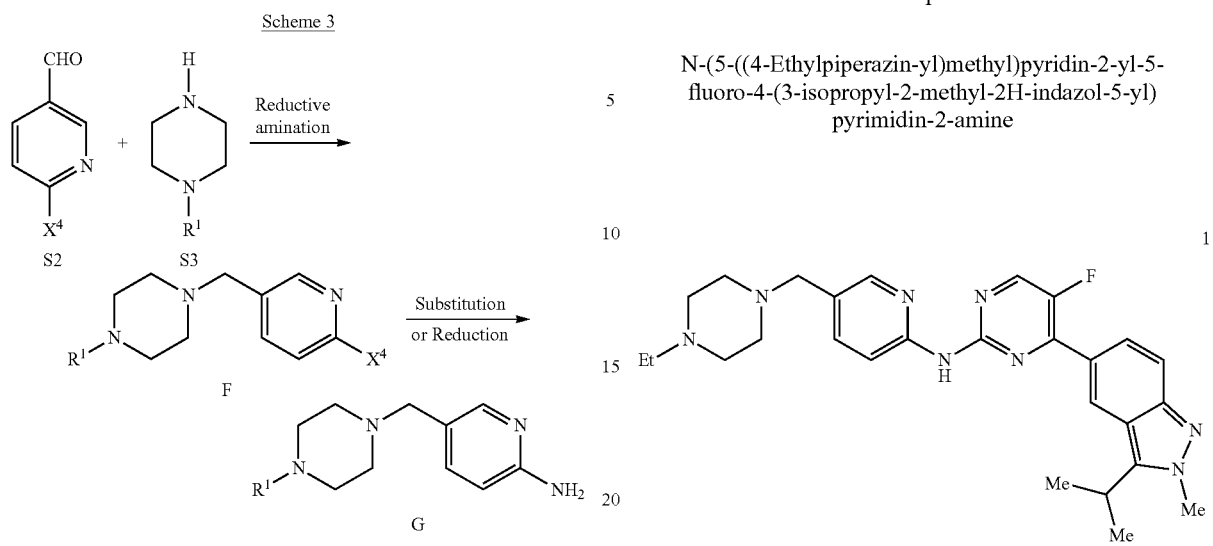

4. Synthesis of Compounds of Formula (I) (Scheme 4)

Coupling of the pyrimidine-substituted indazole intermediate E with the 2-amino-5-piperazinemethyl-pyridine intermediate G in the presence of a catalyst (e.g., palladium catalyst) provides the compound of formula (I).

Scheme 4

EXAMPLES

The following non-limiting Examples further illustrate certain aspects of the present invention. These compounds are prepared according to the general Synthetic Schemes described above.

Example 1

N-(5-((4-Ethylpiperazin-yl)methyl)pyridin-2-yl-5-fluoro-4-(3-isopropyl-2-methyl-2H-indazol-5-yl)pyrimidin-2-amine

Synthesis of Compound 1

As an illustrated example, the synthesis of intermediates E, intermediate G, and Compound 1 are depicted in Schemes 5-7, respectively. In the following reaction schemes some specific reagents or reaction conditions are provided solely for better understanding, but such specific reagents or conditions are not intended to be limiting whatsoever. As a person of skill in the art would appreciate, any specific step of the reaction scheme could be accomplished using a variety of equivalent conditions in various aspects, such as reagents, temperature, catalysts, and/or solvents, etc.

Scheme 5

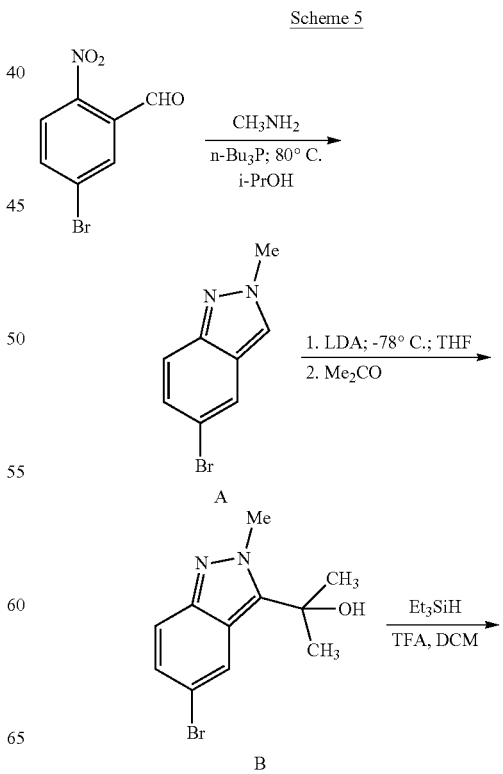

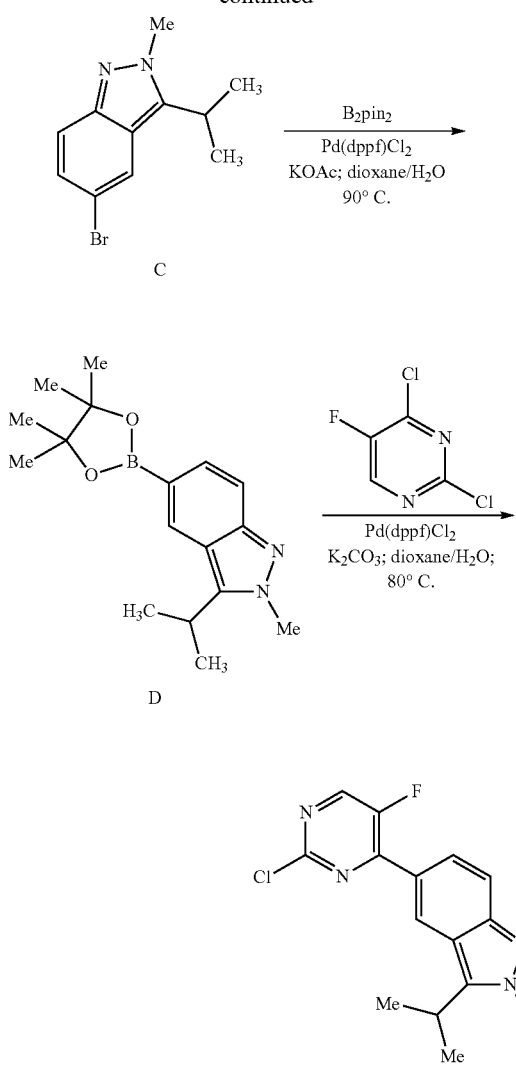

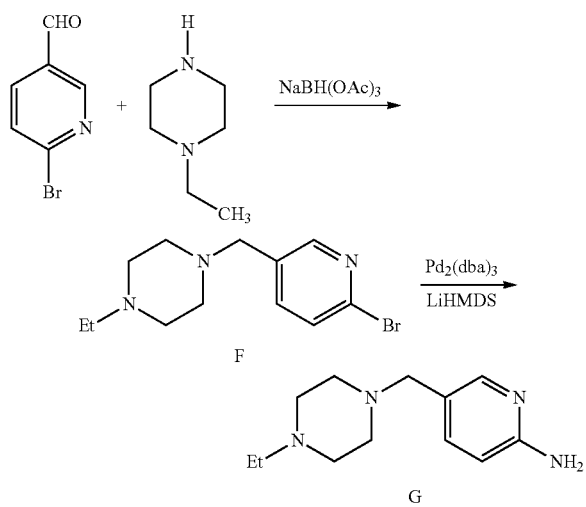

Scheme 6

Scheme 7

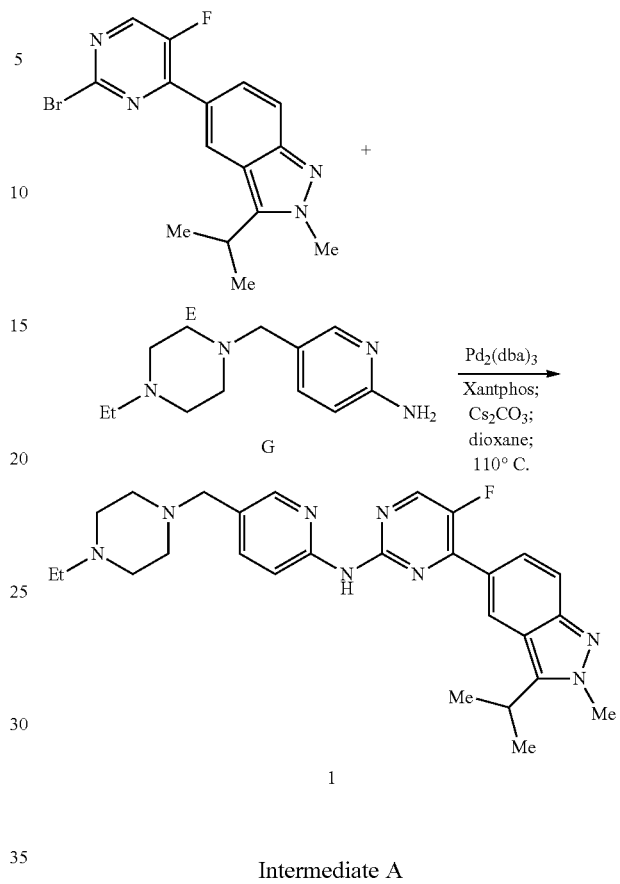

Intermediate A

Into a 500-mL round-bottom flask purged and maintained with an inert atmosphere of nitrogen were placed 5-bromo-2-nitrobenzaldehyde (30.0 g, 130.4 mmol, 1.0 equiv.), methanamine (71.5 mL, 1.1 equiv.), and propan-2-ol (300 mL). The resulting solution was stirred for 4 h at 80° C. The mixture was cooled to rt and tributylphosphine (98 mL, 3.0 equiv.) was added. The resulting solution was stirred for 12 h at 80° C. and then extracted with 500 mL of ethyl acetate. The resulting mixture was washed sequentially with 300 mL of NH$_4$Cl (aq.) and 300 mL of brine. The mixture was dried over anhydrous sodium sulfate and concentrated under vacuum. The residue was applied onto a silica gel column and eluted with ethyl acetate/petroleum ether (1:4). This resulted in 32 g (crude) of 5-bromo-2-methyl-2H-indazole A as a red oil: MS m/z MH$^+$=211

Intermediate B

Into a 1 L 3-necked round-bottom flask purged and maintained with an inert atmosphere of nitrogen were placed 5-bromo-2-methyl-2H-indazole A (32.0 g, 128.9 mmol, 1.0 equiv., 85%) in tetrahydrofuran (300 mL). To the solution was added LDA (97.5 mL, 1.5 equiv., 2 M) at −78° C. The solution was stirred at 0-5° C. for 10 min, then cooled to −78° C. To the solution was added propan-2-one (11.3 g, 194.7 mmol, 1.5 equiv.). The resulting solution was stirred for 12 h at 25° C. The reaction was then quenched with 100 mL of aqueous sodium bicarbonate. The resulting solution was extracted with 3×500 mL of ethyl acetate and the organic layers combined, dried with anhydrous Na$_2$SO$_4$, and filtered. The filtrate was concentrated under vacuum, and the residue was applied onto a silica gel column and eluted with ethyl acetate/petroleum ether (1:10 to 1:2). This resulted in 20 g (58%) of 2-(5-bromo-2-methyl-2H-indazol-3-yl)propan-2-ol B as a yellow oil: MS m/z $M^+$=269

Intermediate C

Into a 500-mL round-bottom flask were placed 2-(5-bromo-2-methyl-2H-indazol-3-yl)propan-2-ol B (20.0 g, 74.3 mmol, 1.0 equiv.), triethylsilane (86.6 g, 744.4 mmol, 10.0 equiv.), trifluoroacetic acid (85.0 g, 752.0 mmol, 10.0 equiv.), and dichloromethane (200 mL). The resulting solution was stirred for 12 h at 25° C. The resulting mixture was concentrated under vacuum. The solution was adjusted to pH 8 with sodium bicarbonate (aq, 2 M). The resulting solution was extracted with 3×100 mL of ethyl acetate, and the organic layers combined and washed with 1×100 mL of brine. The mixture was dried with anhydrous $Na_2SO_4$, filtered, and concentrated under vacuum. The residue was applied onto a silica gel column and eluted with ethyl acetate/petroleum ether (1:20 to 1:10). This resulted in 8 g (43%) of 5-bromo-2-methyl-3-(propan-2-yl)-2H-indazole C as a yellow oil: MS $[M+1]^+$=253 & 255 and $[M+CH_3CN+H]^+$=294 &296

Intermediate D

Into a 100 mL round-bottom flask purged and maintained with an inert atmosphere of nitrogen were placed 5-bromo-2-methyl-3-(propan-2-yl)-2H-indazole (1.9 g, 7.5 mmol, 1.0 equiv.), 4,4,5,5-tetramethyl-2-(tetramethyl-1,3,2-dioxaborolan-2-yl)-1,3,2-dioxaborolane (2.3 g, 9.0 mmol, 1.2 equiv.), KOAc (1.47 g, 15.0 mmol, 2.0 equiv.), 1,4-dioxane (40 mL), and water (10 mL). To the solution was added $Pd(dppf)Cl_2$ (612 mg, 0.75 mmol, 0.1 equiv.). The resulting solution was stirred for 12 h at 90° C., and then cooled to room temperature and concentrated under vacuum. The residue was applied onto a silica gel column and eluted with ethyl acetate/petroleum ether (1:5). This resulted in 2.5 g (crude) of 2-methyl-3-(propan-2-yl)-5-(tetramethyl-1,3,2-dioxaborolan-2-yl)-2H-indazole D as a white solid: MS m/z $MH^+$=301

Intermediate E

Into a 100-mL round-bottom flask purged and maintained with an inert atmosphere of nitrogen were placed 2-methyl-3-(propan-2-yl)-5-(tetramethyl-1,3,2-dioxaborolan-2-yl)-2H-indazole (2.5 g, 7.5 mmol, 1.0 equiv., 90%), 2,4-dichloro-5-fluoropyrimidine (1.7 g, 9.9 mmol, 1.2 equiv.), potassium carbonate (2.3 g, 16.7 mmol, 2.0 equiv.), 1,4-dioxane (40 mL), and water (10 mL). To the solution was added $Pd(dppf)Cl_2$ (680 mg, 0.83 mmol, 0.10 equiv.). The resulting solution was stirred for 2 h at 80° C., and then cooled to room temperature and concentrated under vacuum. The residue was applied onto a silica gel column and eluted with ethyl acetate/petroleum ether (1:2). This resulted in 1.2 g (48%) of 5-(2-chloro-5-fluoropyrimidin-4-yl)-2-methyl-3-(propan-2-yl)-2H-indazole E as an off-white solid: MS m/z $MH^+$=305; $^1H$ NMR (300 MHz, $CDCl_3$, ppm): δ 1.58 (d, 6H), 3.48-3.57 (m, 1H), 4.19 (s, 3H), 7.24 (d, 1H), 8.03-8.07 (m, 1H), 8.47 (d, 1H), 8.68 (s, 1H).

Intermediate F $NaBH(OAc)_3$ (14.4 g, 68.0 mmol, 1.1 equiv.) was added portionwise over 30 min to a solution of N-ethyl piperazine (7.7 g, 67.5 mmol, 1.1 equiv.) and 6-bromopyridine-3-carbaldehyde (11.6 g, 62.5 mmol, 1.0 equiv.) in 150 mL of methylene chloride. The reaction mixture was stirred for 48 h, then diluted with $CH_2Cl_2$ and excess 2N NaOH (aq.). The layers were separated, and the aqueous phase was extracted with $CH_2Cl_2$. The $CH_2Cl_2$ extracts were combined, dried ($Na_2SO_4$), and concentrated to yield 1-(6-bromo-pyridin-3-ylmethyl)-4-ethyl-piperazine F as an oil: MS m/z $MH^+$=285

Intermediate G

Lithium bis(trimethylsilyl)amide (LiHMDS) (1M solution in THF, 12.7 mL, 12.7 mmol, 1.2 equiv) was added to a solution of intermediate F (3.0 g, 10.6 mmol, 1.0 equiv.), dicyclohexylphosphinobiphenyl (0.227 g, 0.64 mmol, 0.06 equiv.), and $Pd_2(dba)_3$ (0.291 g, 0.32 mmol, 0.03 equiv.) in 15 mL of THF. The mixture was heated at 50° C. for 3 h, then cooled to room temperature, and filtered through a Dicalite® filtering medium. The filtrate was concentrated and the residue was taken up in $CH_2Cl_2$ and extracted twice with 10% HCl (aq.). The HCl extracts were combined and washed with EtOAc, and the aqueous phase was basified with 1.0 N NaOH, and then extracted four times with $CH_2Cl_2$. The organic extracts were combined, dried over $Na_2SO_4$ and concentrated to yield 1.2 g of 5-(4-ethyl-piperazinyl-1-ylmethyl)-pyridin-2-ylamine G as a tan solid: MS m/z $MH^+$=221.

Compound 1

A mixture of 5-(2-chloro-5-fluoropyrimidin-4-yl)-2-methyl-3-(propan-2-yl)-2H-indazole (E) (700 mg 2.3 mmol, 1.3 equiv.), 5-((4-ethylpiperazin-1-yl)methylpyridin-2-amine (G) (389 mg, 1.8 mmol, 1.0 equiv.), $Cs_2CO_3$ (2.3 g, 7.2 mmol, 4.0 equiv.), $Pd_2(dba)_3$ (0.164 g, 0.18 mmol, 0.1 equiv.) and Xantphos (0.104 g, 0.18 mmol, 0.1 equiv.) in 10 mL of 1,4-dioxane was degassed with $N_2$, then heated while stirring at 110° C. for 4 h. The mixture was cooled to room temperature, then filtered through a Dicalite® filtering medium, and the filter pad was washed thoroughly with $CH_2Cl_2$. The filtrate was concentrated, and the residue was purified by column chromatography on silica gel using a $CH_2Cl_2$-2% $NH_3$/MeOH gradient to afford 0.475 g of N-(5-((4-ethylpiperazin-yl)methyl)pyridin-2-yl-5-fluoro-4-(3-isopropyl-2-methyl-2H-indazol-5-yl)pyrimidin-2-amine (1). MS m/z $MH^+$ 489; $^1H$ NMR (300 MHz, $CDCl_3$, ppm): δ 0.97 (t, 3H, J=7.1 Hz), 1.51 (d, 2H, J=7.0 Hz), 2.27-2.51 (overlapping m, 10H), 3.33 (s, 3H), 3.54-3.68 (m, 1H), 4.15 (s, 3H), 7.64-8.71 (overlapping m, 7H), 10.00 (s, 1H).

Compounds 1 and other selected examples (Compounds 2-31) of the present invention are listed in Table 1, all of which are or can be prepared according to the methods described above.

TABLE 1

| Example | Structure | Name |
|---|---|---|
| 1 | 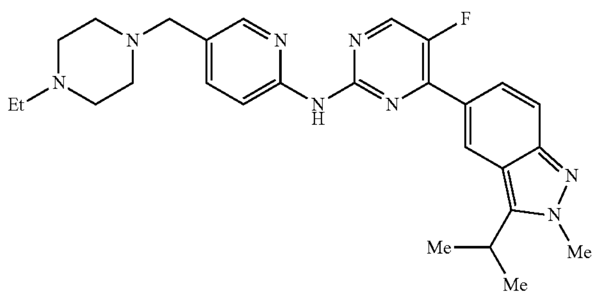 [SMILES: CCN1CCN(Cc2ccc(Nc3ncc(F)c(-c4ccc5nn(C)c(C(C)C)c5c4)n3)nc2)CC1] | N-(5-((4-ethylpiperazin-1-yl)methyl)pyridin-2-yl)-5-fluoro-4-(3-isopropyl-2-methyl-2H-indazol-5-yl)pyrimidin-2-amine |
| 2 | 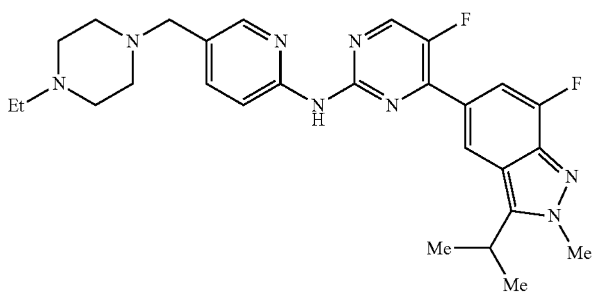 [SMILES: CCN1CCN(Cc2ccc(Nc3ncc(F)c(-c4cc(F)c5nn(C)c(C(C)C)c5c4)n3)nc2)CC1] | N-(5-((4-ethylpiperazin-1-yl)methyl)pyridin-2-yl)-5-fluoro-4-(7-fluoro-3-isopropyl-2-methyl-2H-indazol-5-yl)pyrimidin-2-amine |
| 3 | 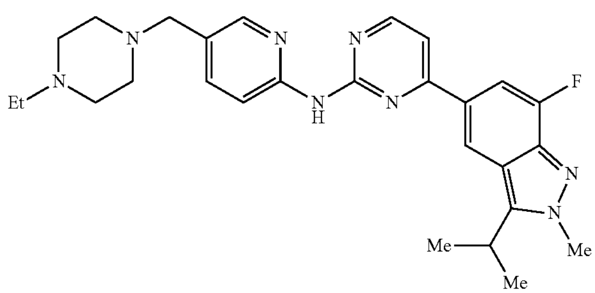 [SMILES: CCN1CCN(Cc2ccc(Nc3nccc(-c4cc(F)c5nn(C)c(C(C)C)c5c4)n3)nc2)CC1] | N-(5-((4-ethylpiperazin-1-yl)methyl)pyridin-2-yl)-4-(7-fluoro-3-isopropyl-2-methyl-2H-indazol-5-yl)pyrimidin-2-amine |
| 4 | 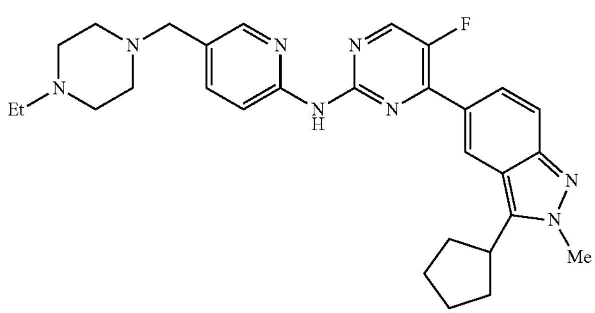 [SMILES: CCN1CCN(Cc2ccc(Nc3ncc(F)c(-c4ccc5nn(C)c(C6CCCC6)c5c4)n3)nc2)CC1] | 4-(3-cyclopentyl-2-methyl-2H-indazol-5-yl)-N-(5-((4-ethylpiperazin-1-yl)methyl)pyridin-2-yl)-5-fluoropyrimidin-2-amine |
| 5 | 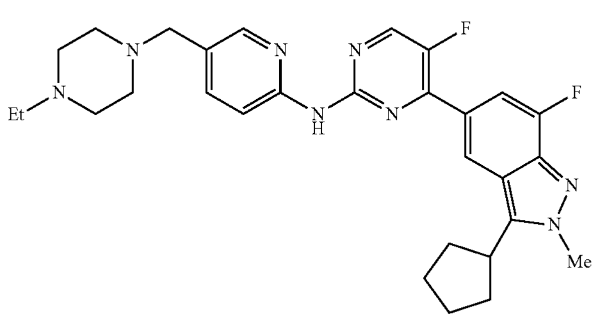 | 4-(3-cyclopentyl-7-fluoro-2-methyl-2H-indazol-5-yl)-N-(5-((4-ethylpiperazin-1-yl)methyl)pyridin-2-yl)-5-fluoropyrimidin-2-amine |

TABLE 1-continued

Selected examples of the compounds

| Example | Structure | Name |
|---------|-----------|------|
| 6 | 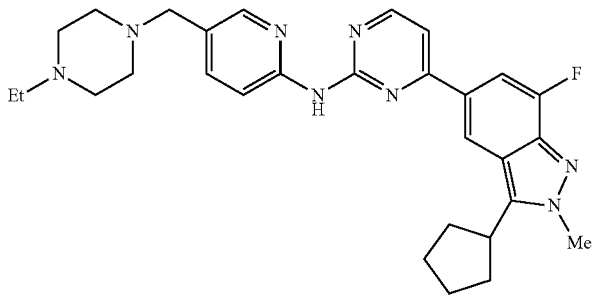 [SMILES: CCN1CCN(Cc2ccc(Nc3nccc(-c4cc(F)c5nn(C)c(C6CCCC6)c5c4)n3)nc2)CC1] | 4-(3-cyclopentyl-7-fluoro-2-methyl-2H-indazol-5-yl)-N-(5-((4-ethylpiperazin-1-yl)methyl)pyridin-2-yl)pyrimidin-2-amine |
| 7 | 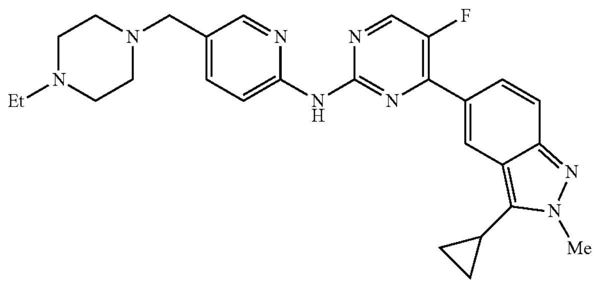 [SMILES: CCN1CCN(Cc2ccc(Nc3ncc(F)c(-c4ccc5nn(C)c(C6CC6)c5c4)n3)nc2)CC1] | 4-(3-cyclopropyl-2-methyl-2H-indazol-5-yl)-N-(5-((4-ethylpiperazin-1-yl)methyl)pyridin-2-yl)-5-fluoropyrimidin-2-amine |
| 8 | 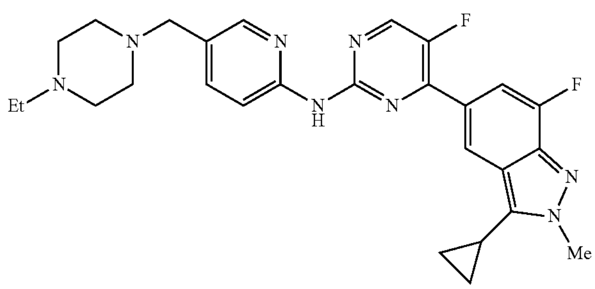 [SMILES: CCN1CCN(Cc2ccc(Nc3ncc(F)c(-c4cc(F)c5nn(C)c(C6CC6)c5c4)n3)nc2)CC1] | 4-(3-cyclopropyl-7-fluoro-2-methyl-2H-indazol-5-yl)-N-(5-((4-ethylpiperazin-1-yl)methyl)pyridin-2-yl)-5-fluoropyrimidin-2-amine |
| 9 | 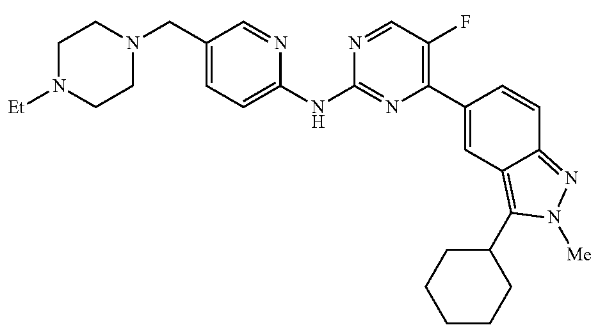 [SMILES: CCN1CCN(Cc2ccc(Nc3ncc(F)c(-c4ccc5nn(C)c(C6CCCCC6)c5c4)n3)nc2)CC1] | 4-(3-cyclohexyl-2-methyl-2H-indazol-5-yl)-N-(5-((4-ethylpiperazin-1-yl)methyl)pyridin-2-yl)-5-fluoropyrimidin-2-amine |
| 10 | 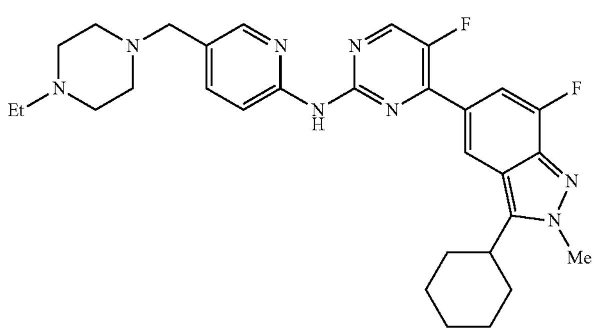 [SMILES: CCN1CCN(Cc2ccc(Nc3ncc(F)c(-c4cc(F)c5nn(C)c(C6CCCCC6)c5c4)n3)nc2)CC1] | 4-(3-cyclohexyl-7-fluoro-2-methyl-2H-indazol-5-yl)-N-(5-((4-ethylpiperazin-1-yl)methyl)pyridin-2-yl)-5-fluoropyrimidin-2-amine |

TABLE 1-continued

Selected examples of the compounds

| Example | Structure | Name |
|---|---|---|
| 11 | 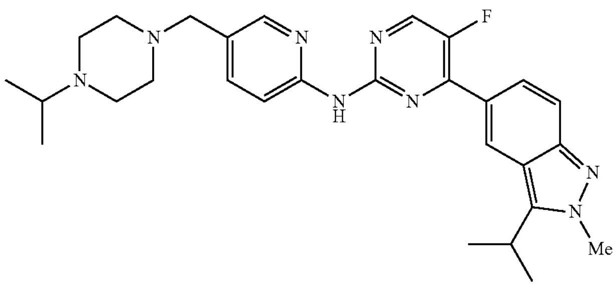 [SMILES: CC(C)c1c2cc(-c3nc(Nc4ccc(CN5CCN(C(C)C)CC5)cn4)ncc3F)ccc2nn1C] | 5-fluoro-4-(3-isopropyl-2-methyl-2H-indazol-5-yl)-N-(5-((4-isopropylpiperazin-1-yl)methyl)pyridin-2-yl)pyrimidin-2-amine |
| 12 | 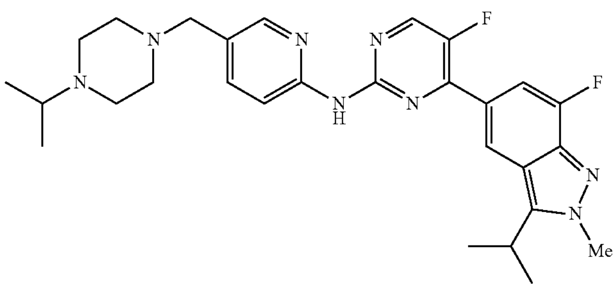 [SMILES: CC(C)c1c2cc(-c3nc(Nc4ccc(CN5CCN(C(C)C)CC5)cn4)ncc3F)cc(F)c2nn1C] | 5-fluoro-4-(7-fluoro-3-isopropyl-2-methyl-2H-indazol-5-yl)-N-(5-((4-isopropylpiperazin-1-yl)methyl)pyridin-2-yl)pyrimidin-2-amine |
| 13 | 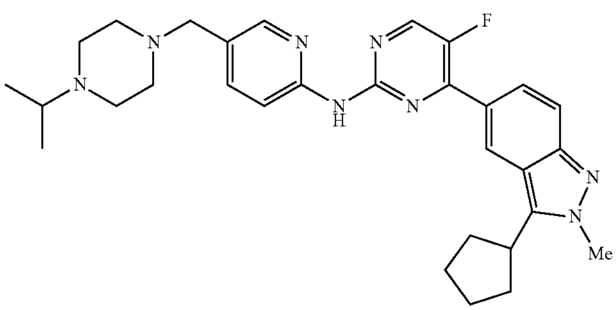 [SMILES: CC(C)N1CCN(Cc2ccc(Nc3ncc(F)c(-c4ccc5nn(C)c(C6CCCC6)c5c4)n3)nc2)CC1] | 4-(3-cyclopentyl-2-methyl-2H-indazol-5-yl)-5-fluoro-N-(5-((4-isopropylpiperazin-1-yl)methyl)pyridin-2-yl)pyrimidin-2-amine |
| 14 | 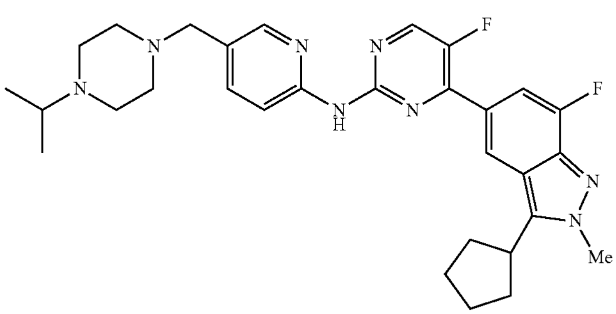 [SMILES: CC(C)N1CCN(Cc2ccc(Nc3ncc(F)c(-c4cc(F)c5nn(C)c(C6CCCC6)c5c4)n3)nc2)CC1] | 4-(3-cyclopentyl-7-fluoro-2-methyl-2H-indazol-5-yl)-5-fluoro-N-(5-((4-isopropylpiperazin-1-yl)methyl)pyridin-2-yl)pyrimidin-2-amine |
| 15 | 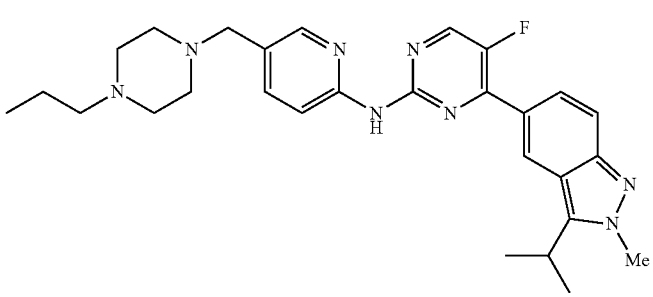 [SMILES: CCCN1CCN(Cc2ccc(Nc3ncc(F)c(-c4ccc5nn(C)c(C(C)C)c5c4)n3)nc2)CC1] | 5-fluoro-4-(3-isopropyl-2-methyl-2H-indazol-5-yl)-N-(5-((4-propylpiperazin-1-yl)methyl)pyridin-2-yl)pyrimidin-2-amine |

TABLE 1-continued

Selected examples of the compounds

| Example | Structure | Name |
|---|---|---|
| 16 | 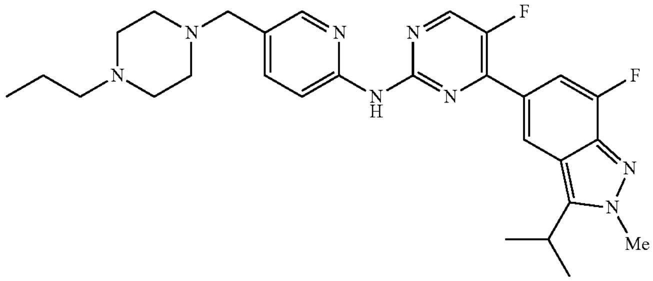 [SMILES: CCCN1CCN(Cc2ccc(Nc3ncc(F)c(-c4cc(F)c5nn(C)c(C(C)C)c5c4)n3)nc2)CC1] | 5-fluoro-4-(7-fluoro-3-isopropyl-2-methyl-2H-indazol-5-yl)-N-(5-((4-propylpiperazin-1-yl)methyl)pyridin-2-yl)pyrimidin-2-amine |
| 17 | 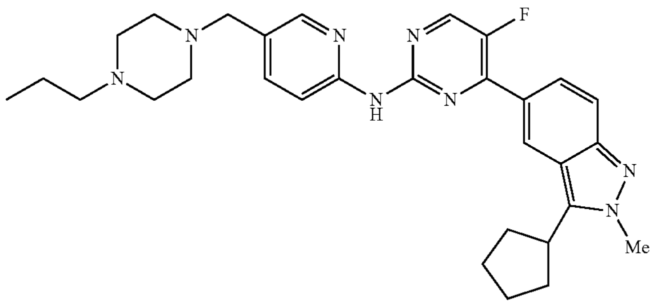 [SMILES: CCCN1CCN(Cc2ccc(Nc3ncc(F)c(-c4ccc5nn(C)c(C6CCCC6)c5c4)n3)nc2)CC1] | 4-(3-cyclopentyl-2-methyl-2H-indazol-5-yl)-5-fluoro-N-(5-((4-propylpiperazin-1-yl)methyl)pyridin-2-yl)pyrimidin-2-amine |
| 18 | 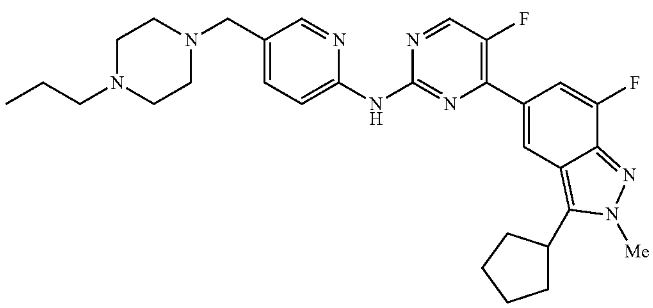 [SMILES: CCCN1CCN(Cc2ccc(Nc3ncc(F)c(-c4cc(F)c5nn(C)c(C6CCCC6)c5c4)n3)nc2)CC1] | 4-(3-cyclopentyl-7-fluoro-2-methyl-2H-indazol-5-yl)-5-fluoro-N-(5-((4-propylpiperazin-1-yl)methyl)pyridin-2-yl)pyrimidin-2-amine |
| 19 | 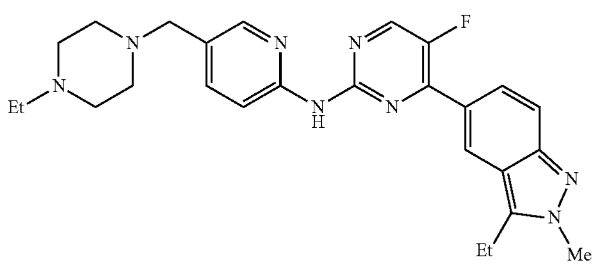 [SMILES: CCc1c2cc(-c3nc(Nc4ccc(CN5CCN(CC)CC5)cn4)ncc3F)ccc2nn1C] | 4-(3-ethyl-2-methyl-2H-indazol-5-yl)-N-(5-((4-ethylpiperazin-1-yl)methyl)pyridin-2-yl)-5-fluoropyrimidin-2-amine |
| 20 | 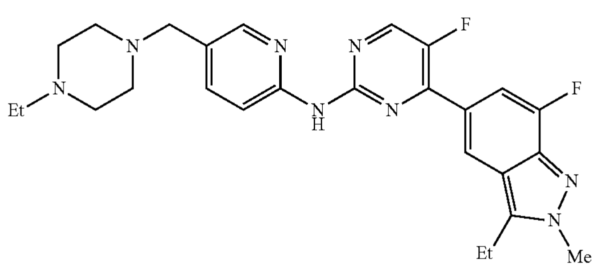 [SMILES: CCc1c2cc(-c3nc(Nc4ccc(CN5CCN(CC)CC5)cn4)ncc3F)cc(F)c2nn1C] | 4-(3-ethyl-7-fluoro-2-methyl-2H-indazol-5-yl)-N-(5-((4-ethylpiperazin-1-yl)methyl)pyridin-2-yl)-5-fluoropyrimidin-2-amine |

TABLE 1-continued

Selected examples of the compounds

| Example | Structure | Name |
|---|---|---|
| 21 | 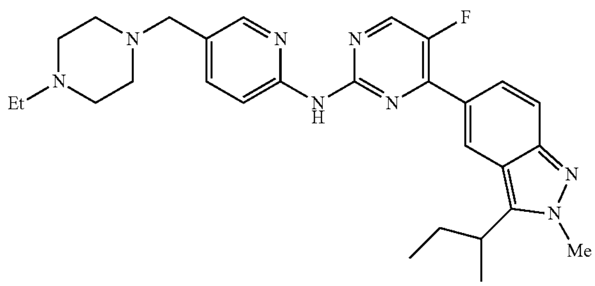 [SMILES: CCC(C)c1c2cc(-c3nc(Nc4ccc(CN5CCN(CC)CC5)cn4)ncc3F)ccc2nn1C] | 4-(3-(sec-butyl)-2-methyl-2H-indazol-5-yl)-N-(5-((4-ethylpiperazin-1-yl)methyl)pyridin-2-yl)-5-fluoropyrimidin-2-amine |
| 22 | 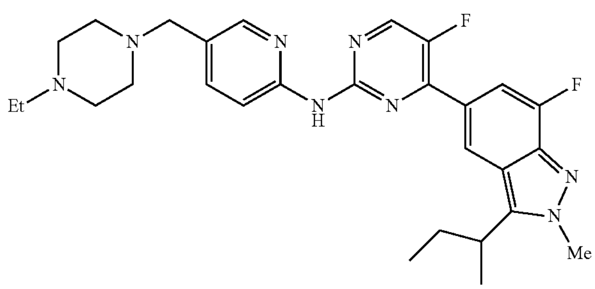 [SMILES: CCC(C)c1c2cc(-c3nc(Nc4ccc(CN5CCN(CC)CC5)cn4)ncc3F)cc(F)c2nn1C] | 4-(3-(sec-butyl)-7-fluoro-2-methyl-2H-indazol-5-yl)-N-(5-((4-ethylpiperazin-1-yl)methyl)pyridin-2-yl)-5-fluoropyrimidin-2-amine |
| 23 | 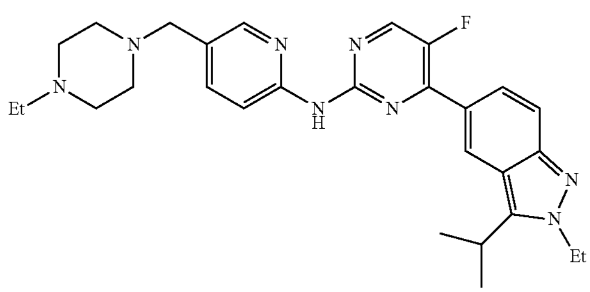 [SMILES: CCN1CCN(Cc2ccc(Nc3ncc(F)c(-c4ccc5nn(CC)c(C(C)C)c5c4)n3)nc2)CC1] | 4-(2-ethyl-3-isopropyl-2H-indazol-5-yl)-N-(5-((4-ethylpiperazin-1-yl)methyl)pyridin-2-yl)-5-fluoropyrimidin-2-amine |
| 24 | 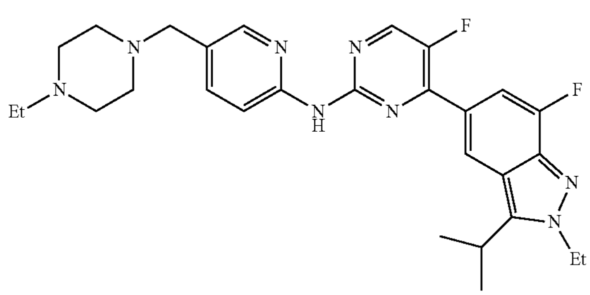 [SMILES: CCN1CCN(Cc2ccc(Nc3ncc(F)c(-c4cc(F)c5nn(CC)c(C(C)C)c5c4)n3)nc2)CC1] | 4-(2-ethyl-7-fluoro-3-isopropyl-2H-indazol-5-yl)-N-(5-((4-ethylpiperazin-1-yl)methyl)pyridin-2-yl)-5-fluoropyrimidin-2-amine |
| 25 | 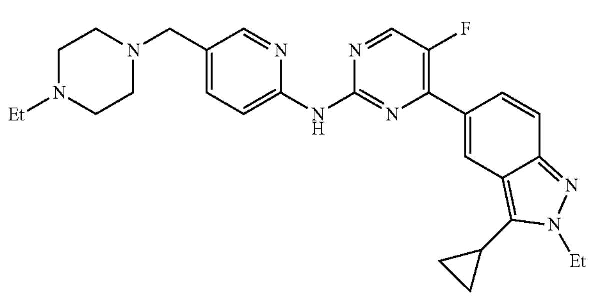 [SMILES: CCN1CCN(Cc2ccc(Nc3ncc(F)c(-c4ccc5nn(CC)c(C6CC6)c5c4)n3)nc2)CC1] | 4-(3-cyclopropyl-2-ethyl-2H-indazol-5-yl)-N-(5-((4-ethylpiperazin-1-yl)methyl)pyridin-2-yl)-5-fluoropyrimidin-2-amine |

TABLE 1-continued

Selected examples of the compounds

| Example | Structure | Name |
|---|---|---|
| 26 | 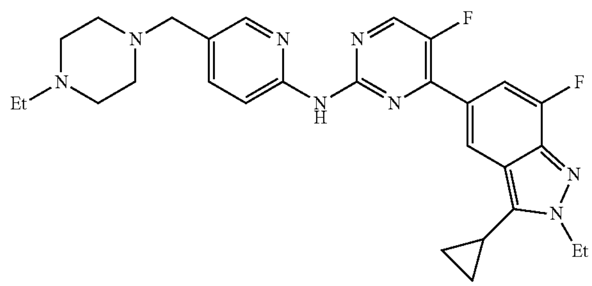 [SMILES: CCN1CCN(Cc2ccc(Nc3ncc(F)c(-c4cc(F)c5nn(CC)c(C6CC6)c5c4)n3)nc2)CC1] | 4-(3-cyclopropyl-2-ethyl-7-fluoro-2H-indazol-5-yl)-N-(5-((4-ethylpiperazin-1-yl)methyl)pyridin-2-yl)-5-fluoropyrimidin-2-amine |
| 27 | 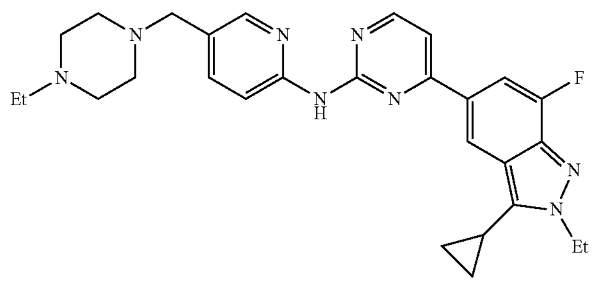 [SMILES: CCN1CCN(Cc2ccc(Nc3nccc(-c4cc(F)c5nn(CC)c(C6CC6)c5c4)n3)nc2)CC1] | 4-(3-(cyclopropylmethyl)-2-methyl-2H-indazol-5-yl)-N-(5-((4-ethylpiperazin-1-yl)methyl)pyridin-2-yl)-5-fluoropyrimidin-2-amine |
| 28 | 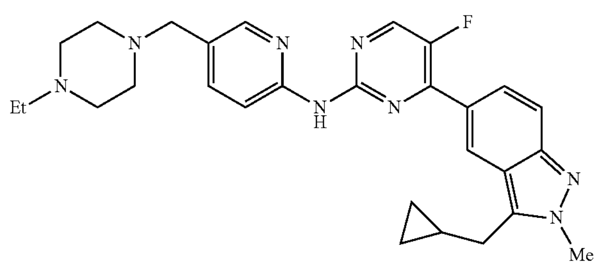 [SMILES: CCN1CCN(Cc2ccc(Nc3ncc(F)c(-c4ccc5nn(C)c(CC6CC6)c5c4)n3)nc2)CC1] | 4-(3-(cyclopropylmethyl)-7-fluoro-2-methyl-2H-indazol-5-yl)-N-(5-((4-ethylpiperazin-1-yl)methyl)pyridin-2-yl)-5-fluoropyrimidin-2-amine |
| 29 | 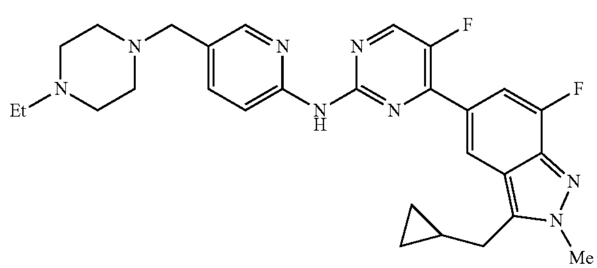 [SMILES: CCN1CCN(Cc2ccc(Nc3ncc(F)c(-c4cc(F)c5nn(C)c(CC6CC6)c5c4)n3)nc2)CC1] | 4-(3-cyclopropyl-2-ethyl-7-fluoro-2H-indazol-5-yl)-N-(5-((4-ethylpiperazin-1-yl)methyl)pyridin-2-yl)pyrimidin-2-amine |
| 30 | 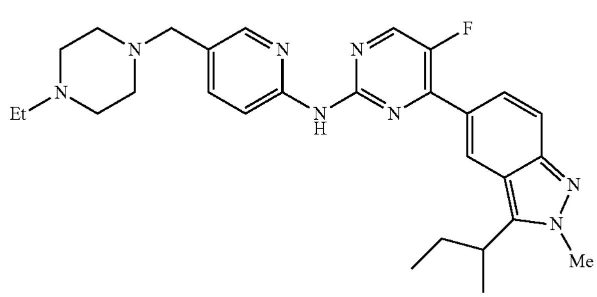 [SMILES: CCC(C)c1c2cc(-c3nc(Nc4ccc(CN5CCN(CC)CC5)cn4)ncc3F)ccc2nn1C] | 4-(3-(sec-butyl)-2-methyl-2H-indazol-5-yl)-N-(5-((4-ethylpiperazin-1-yl)methyl)pyridin-2-yl)-5-fluoropyrimidin-2-amine |

TABLE 1-continued

Selected examples of the compounds

| Example | Structure | Name |
|---|---|---|
| 31 | 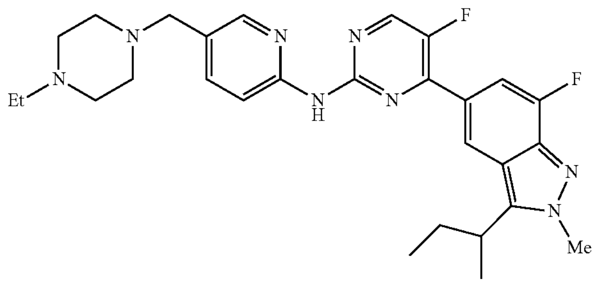 [SMILES: CCC(C)c1c2cc(-c3nc(Nc4ccc(CN5CCN(CC)CC5)cn4)ncc3F)cc(F)c2nn1C] | 4-(3-(sec-butyl)-7-fluoro-2-methyl-2H-indazol-5-yl)-N-(5-((4-ethylpiperazin-1-yl)methyl)pyridin-2-yl)-5-fluoropyrimidin-2-amine |

Biological Assays

Compounds of the formula I are novel CDK4/6 inhibitors that have been or can be evaluated for their activity according to the procedures described below.

Biochemical Assay

Cyclin D1 was added to freshly prepared reaction buffer [20 mM Hepes (pH 7.5), 10 mM $MgCl_2$, 1 mM EGTA, 0.02% Brij 35, 0.02 mg/mL BSA, 0.1 mM $Na_3VO_4$, 2 mM DTT, 1% DMSO]. CDK4 or CDK6 was delivered to the substrate solution and gently mixed. Compounds were tested in a 10-dose $IC_{50}$ mode with 3-fold dilution starting at 10 μM. The compounds, diluted in DMSO, were added into the kinase reaction mixture by Acoustic technology (Echo550; nanoliter range) and incubated for 20 minutes at room temperature. 33P-ATP (1 μM) was added to the reaction mixture to initiate the reaction. The kinase reaction was incubated for 2 hours at room temperature. The reactions were spotted onto P81 ion exchange paper and the kinase activity detected by filter-binding method. Curves were fitted to a nonlinear regression curve using a four parameter logistic equation (GraphPad Prism). Under these conditions, an $IC_{50}$ value of <1.0 nM was determined for 1 in both CDK4 and CDK6 assays.

Cell Assay

The MCF7 human tumor cells were seeded in a clear polystyrene 96-well microculture plate (Corning® Costar® 96-well flat bottom plate, Cat. #3997) in a total volume of 90 μL/well. After 24 hours of incubation in a humidified incubator at 37° C. with 5% $CO_2$ and 95% air, 10 μL of 10×, serially diluted 1 in growth medium was added to each well in duplicate (10 point dose response). After 72 hours of culture in a humidified incubator at 37° C., in an atmosphere of 5% $CO_2$ and 95% air, the plated cells and Cell Titer-Glo® (Promega G7571) reagents were brought to room temperature to equilibrate for 30 minutes. 100 μL of Cell Titer-Glo® reagent was added to each well. The plate was shaken for two minutes and then left to equilibrate for ten minutes. The medium/Cell Titer Glo® reagent was transferred to a white polystyrene 96-well microculture plate (Corning® Costar® 96-well flat bottom plate, Cat. #3917) before reading luminescence on the Tecan GENios microplate reader. Percent inhibition of cell growth was calculated relative to untreated control wells. All tests were performed in duplicate at each concentration level. The $IC_{50}$ value for the test agents was estimated using Prism 6.05 by curve-fitting the data using the following four parameter-logistic equation:

$$Y = \frac{Top - Bottom}{1 + (X/IC_{50})^n} + Bottom$$

where Top is the maximal % of control absorbance, Bottom is the minimal % of control absorbance at the highest agent concentration, Y is the % of control absorbance, X is the agent concentration, $IC_{50}$ is the concentration of agent that inhibits cell growth by 50% compared to the control cells, and n is the slope of the curve. Under these conditions, an $IC_{50}$ value of <2 μM was determined for 1.

Table 2 summarizes biochemical and MCF7 cell-based data for the three reported CDK4/6 inhibitors 32, 33 and 34. The data was obtained under assay conditions described herein.

TABLE 2
Biochemical and cell data for known inhibitors of CDK4/6
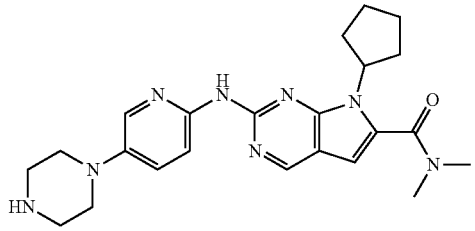 [SMILES: CN(C)C(=O)c1cc2cnc(Nc3ccc(N4CCNCC4)cn3)nc2n1C1CCCC1]
32
IC$_{50}$ (μM)
| | |
|---|---|
| MCF7 cells | 10 |
| CDK4 biochemical assay | <0.005 |
| CDK6 biochemical assay | <0.002 |
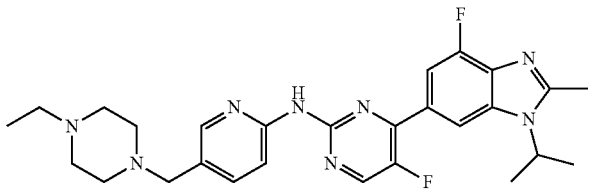 [SMILES: CCN1CCN(Cc2ccc(Nc3ncc(F)c(-c4cc(F)c5nc(C)n(C(C)C)c5c4)n3)nc2)CC1]
33
IC$_{50}$ (μM)
| | |
|---|---|
| MCF7 cells | <2 |
| CDK4 biochemical assay | <0.001 |
| CDK6 biochemical assay | <0.001 |
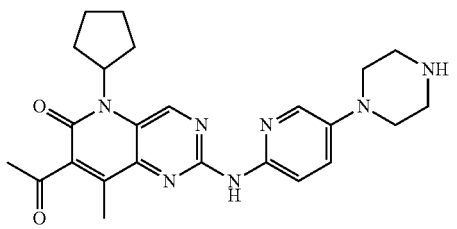 [SMILES: CC(=O)c1c(C)c2nc(Nc3ccc(N4CCNCC4)cn3)ncc2n(C2CCCC2)c1=O]
34
IC$_{50}$ (μM)
| | |
|---|---|
| MCF7 cells | 10 |
| CDK4 biochemical assay | <0.001 |
| CDK6 biochemical assay | <0.002 |

It will be understood by those of skill in the art that numerous and various modifications can be made to the compounds, compositions, and/or methods of the present invention without departing from the spirit of the invention. Therefore, the various embodiments of the present invention described herein are illustrative only, and are not intended to limit the scope of the invention in any way. All references cited herein are incorporated by reference in their entirety.

What is claimed is:

1. A compound of formula (I)

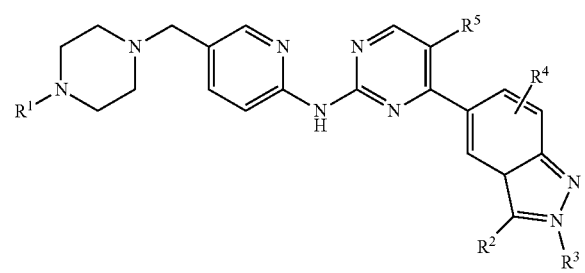

(I)

or a pharmaceutically acceptable salt, solvate, or prodrug thereof, wherein:

$R^1$ is hydrogen, $C_1$-$C_8$ alkyl, or $C_3$-$C_7$ cycloalkyl;

$R^2$ and $R^3$ are each independently hydrogen, $C_1$-$C_8$ alkyl, $C_3$-$C_7$ cycloalkyl, or $C_3$-$C_7$ cycloalkylmethyl;

$R^4$ is hydrogen, halogen, $C_1$-$C_8$ alkyl, or $C_3$-$C_7$ cycloalkyl; and $R^5$ is hydrogen or halogen.

2. The compound of claim 1, or a pharmaceutically acceptable salt, solvate, or prodrug thereof, wherein $R^1$ is $C_1$-$C_6$ alkyl.

3. The compound of claim 1, or a pharmaceutically acceptable salt, solvate, or prodrug thereof, wherein $R^1$ is methyl, ethyl, propyl, or isopropyl.

4. The compound of claim 2, or a pharmaceutically acceptable salt, solvate, or prodrug thereof, wherein $R^2$ is $C_1$-$C_6$ alkyl, $C_3$-$C_6$ cycloalkyl, or $C_3$-$C_6$ cycloalkylmethyl.

5. The compound of claim 3, or a pharmaceutically acceptable salt, solvate, or prodrug thereof, wherein $R^2$ is methyl, ethyl, propyl, isopropyl, cyclopropyl, cyclopentyl, cyclopropylmethyl, or cyclopentylmethyl.

6. The compound of claim 4, or a pharmaceutically acceptable salt, solvate, or prodrug thereof, wherein $R^3$ is $C_1$-$C_6$ alkyl or $C_3$-$C_6$ cycloalkyl.

7. The compound of claim 5, or a pharmaceutically acceptable salt, solvate, or prodrug thereof, wherein $R^3$ is methyl, ethyl, propyl, isopropyl, or cyclopropyl.

8. The compound of claim 1, or a pharmaceutically acceptable salt, solvate, or prodrug thereof, wherein $R^4$ is located at the 7-position of the indazole ring, characterized by formula Ia:

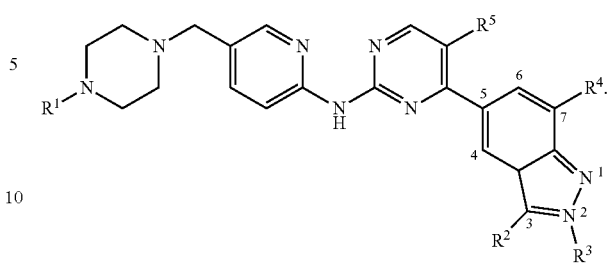

(Ia)

9. The compound of claim 8, or a pharmaceutically acceptable salt, solvate, or prodrug thereof, wherein $R^4$ is hydrogen or halogen.

10. The compound of claim 1, or a pharmaceutically acceptable salt, solvate, or prodrug thereof, wherein $R^5$ is hydrogen or fluoro.

11. The compound of claim 8, or a pharmaceutically acceptable salt, solvate, or prodrug thereof, wherein $R^1$ is methyl or ethyl; $R^2$ is isopropyl, cyclopropyl, cyclopropylmethyl, or cyclopentyl; $R^3$ is methyl or ethyl; $R^4$ is hydrogen or fluoro; and $R^5$ is hydrogen or fluoro.

12. The compound of claim 6, or a pharmaceutically acceptable salt, solvate, or prodrug thereof, selected from the group consisting of:

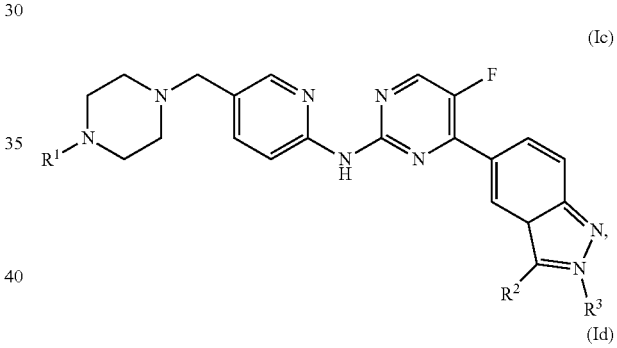

(Ic)

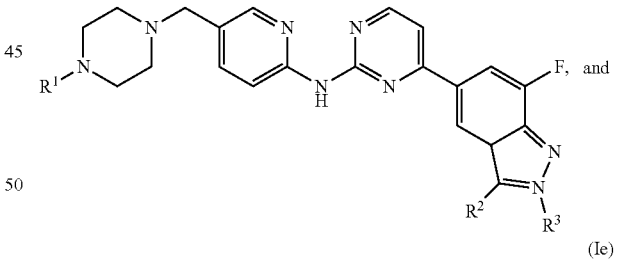

(Id)

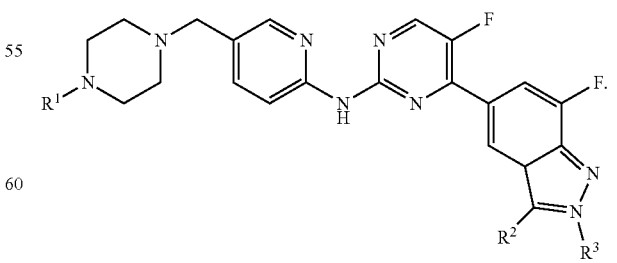

(Ie)

13. The compound of claim 1, or a pharmaceutically acceptable salt, solvate, or prodrug thereof, selected from the list in the table below:

| Compound No. | Structure | Name |
|---|---|---|
| 1 | 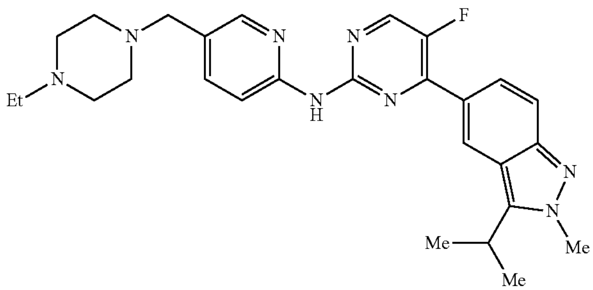 [SMILES: CCN1CCN(Cc2ccc(Nc3ncc(F)c(-c4ccc5nn(C)c(C(C)C)c5c4)n3)nc2)CC1] | N-(5-((4-ethylpiperazin-1-yl)methyl)pyridin-2-yl)-5-fluoro-4-(3-isopropyl-2-methyl-2H-indazol-5-yl)pyrimidin-2-amine |
| 2 | 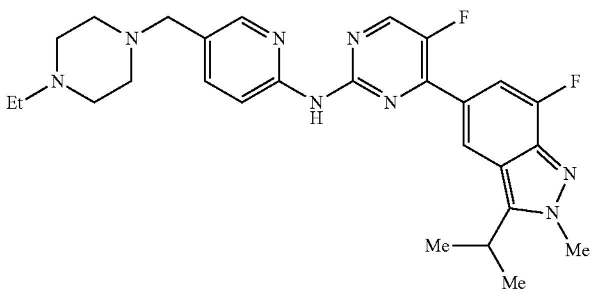 [SMILES: CCN1CCN(Cc2ccc(Nc3ncc(F)c(-c4cc(F)c5nn(C)c(C(C)C)c5c4)n3)nc2)CC1] | N-(5-((4-ethylpiperazin-1-yl)methyl)pyridin-2-yl)-5-fluoro-4-(7-fluoro-3-isopropyl-2-methyl-2H-indazol-5-yl)pyrimidin-2-amine |
| 3 | 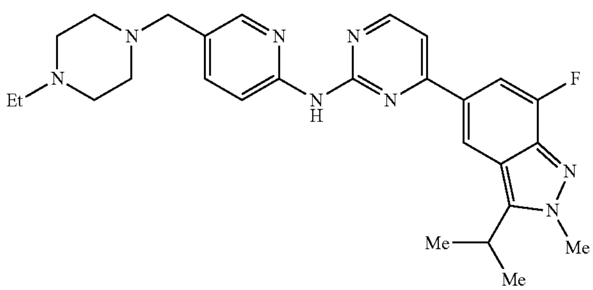 [SMILES: CCN1CCN(Cc2ccc(Nc3nccc(-c4cc(F)c5nn(C)c(C(C)C)c5c4)n3)nc2)CC1] | N-(5-((4-ethylpiperazin-1-yl)methyl)pyridin-2-yl)-4-(7-fluoro-3-isopropyl-2-methyl-2H-indazol-5-yl)pyrimidin-2-amine |
| 4 | 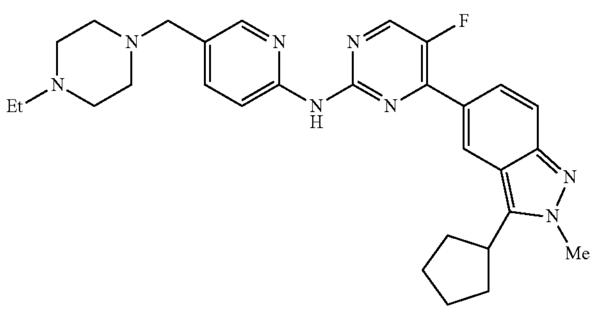 [SMILES: CCN1CCN(Cc2ccc(Nc3ncc(F)c(-c4ccc5nn(C)c(C6CCCC6)c5c4)n3)nc2)CC1] | 4-(3-cyclopentyl-2-methyl-2H-indazol-5-yl)-N-(5-((4-ethylpiperazin-1-yl)methyl)pyridin-2-yl)-5-fluoropyrimidin-2-amine |
| 5 | 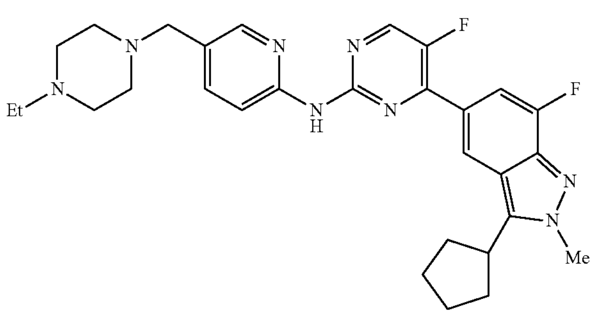 [SMILES: CCN1CCN(Cc2ccc(Nc3ncc(F)c(-c4cc(F)c5nn(C)c(C6CCCC6)c5c4)n3)nc2)CC1] | 4-(3-cyclopentyl-7-fluoro-2-methyl-2H-indazol-5-yl)-N-(5-((4-ethylpiperazin-1-yl)methyl)pyridin-2-yl)-5-fluoropyrimidin-2-amine |

-continued

| Compound No. | Structure | Name |
|---|---|---|
| 6 | 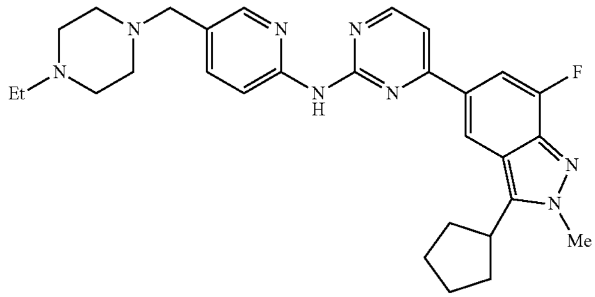 [SMILES: CCN1CCN(Cc2ccc(Nc3nccc(-c4cc(F)c5nn(C)c(C6CCCC6)c5c4)n3)nc2)CC1] | 4-(3-cyclopentyl-7-fluoro-2-methyl-2H-indazol-5-yl)-N-(5-((4-ethylpiperazin-1-yl)methyl)pyridin-2-yl)pyrimidin-2-amine |
| 7 | 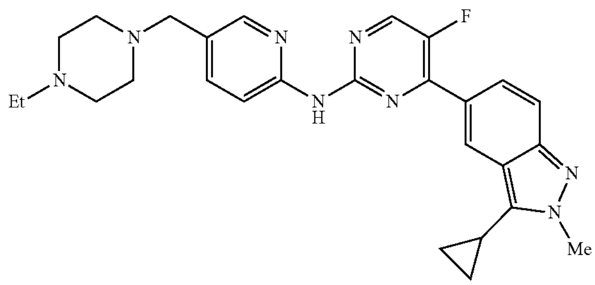 [SMILES: CCN1CCN(Cc2ccc(Nc3ncc(F)c(-c4ccc5nn(C)c(C6CC6)c5c4)n3)nc2)CC1] | 4-(3-cyclopropyl-2-methyl-2H-indazol-5-yl)-N-(5-((4-ethylpiperazin-1-yl)methyl)pyridin-2-yl)-5-fluoropyrimidin-2-amine |
| 8 | 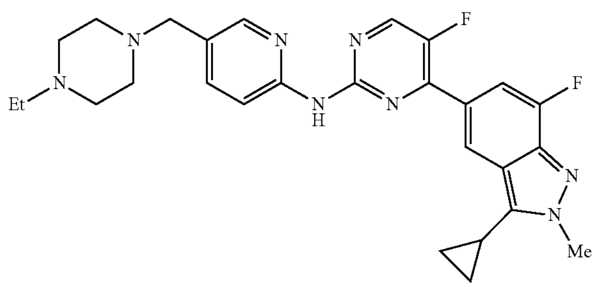 [SMILES: CCN1CCN(Cc2ccc(Nc3ncc(F)c(-c4cc(F)c5nn(C)c(C6CC6)c5c4)n3)nc2)CC1] | 4-(3-cyclopropyl-7-fluoro-2-methyl-2H-indazol-5-yl)-N-(5-((4-ethylpiperazin-1-yl)methyl)pyridin-2-yl)-5-fluoropyrimidin-2-amine |
| 9 | 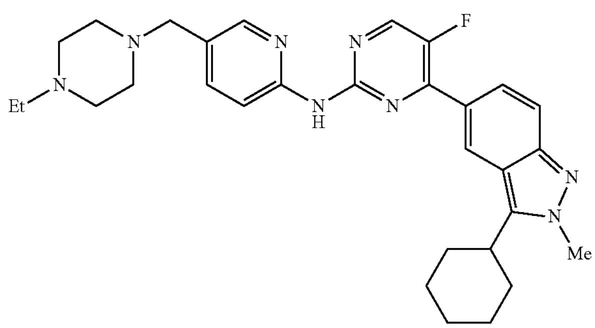 [SMILES: CCN1CCN(Cc2ccc(Nc3ncc(F)c(-c4ccc5nn(C)c(C6CCCCC6)c5c4)n3)nc2)CC1] | 4-(3-cyclohexyl-2-methyl-2H-indazol-5-yl)-N-(5-((4-ethylpiperazin-1-yl)methyl)pyridin-2-yl)-5-fluoropyrimidin-2-amine |
| 10 | 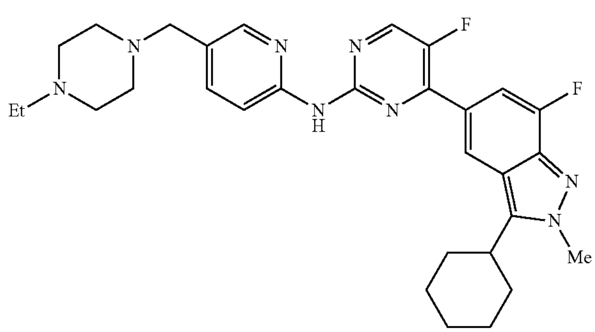 [SMILES: CCN1CCN(Cc2ccc(Nc3ncc(F)c(-c4cc(F)c5nn(C)c(C6CCCCC6)c5c4)n3)nc2)CC1] | 4-(3-cyclohexyl-7-fluoro-2-methyl-2H-indazol-5-yl)-N-(5-((4-ethylpiperazin-1-yl)methyl)pyridin-2-yl)-5-fluoropyrimidin-2-amine |

| Compound No. | Structure | Name |
|---|---|---|
| 11 | 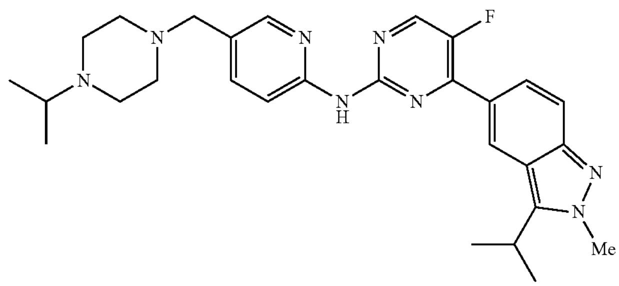 [SMILES: CC(C)c1c2cc(-c3nc(Nc4ccc(CN5CCN(C(C)C)CC5)cn4)ncc3F)ccc2nn1C] | 5-fluoro-4-(3-isopropyl-2-methyl-2H-indazol-5-yl)-N-(5-((4-isopropylpiperazin-1-yl)methyl)pyridin-2-yl)pyrimidin-2-amine |
| 12 | 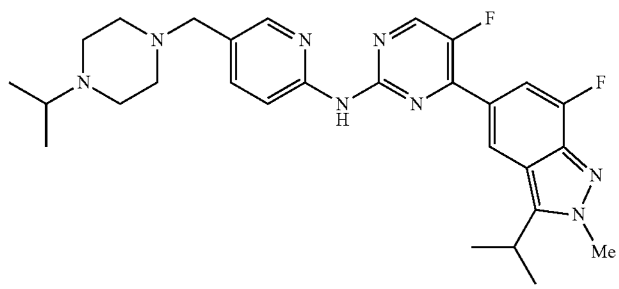 [SMILES: CC(C)c1c2cc(-c3nc(Nc4ccc(CN5CCN(C(C)C)CC5)cn4)ncc3F)cc(F)c2nn1C] | 5-fluoro-4-(7-fluoro-3-isopropyl-2-methyl-2H-indazol-5-yl)-N-(5-((4-isopropylpiperazin-1-yl)methyl)pyridin-2-yl)pyrimidin-2-amine |
| 13 | 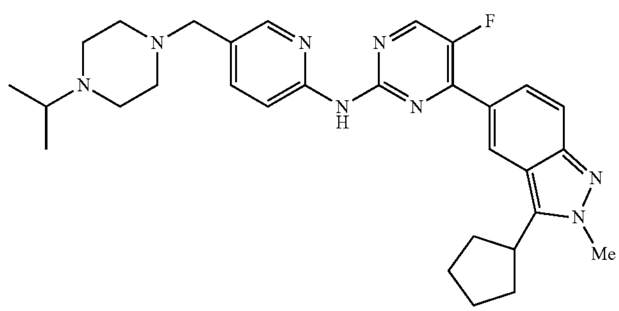 [SMILES: CC(C)N1CCN(Cc2ccc(Nc3ncc(F)c(-c4ccc5nn(C)c(C6CCCC6)c5c4)n3)nc2)CC1] | 4-(3-cyclopentyl-2-methyl-2H-indazol-5-yl)-5-fluoro-N-(5-((4-isopropylpiperazin-1-yl)methyl)pyridin-2-yl)pyrimidin-2-amine |
| 14 | 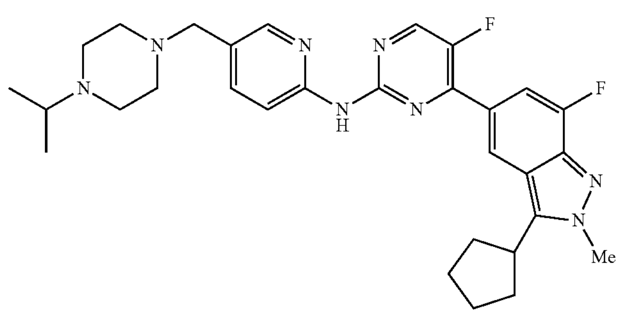 [SMILES: CC(C)N1CCN(Cc2ccc(Nc3ncc(F)c(-c4cc(F)c5nn(C)c(C6CCCC6)c5c4)n3)nc2)CC1] | 4-(3-cyclopentyl-7-fluoro-2-methyl-2H-indazol-5-yl)-5-fluoro-N-(5-((4-isopropylpiperazin-1-yl)methyl)pyridin-2-yl)pyrimidin-2-amine |
| 15 | 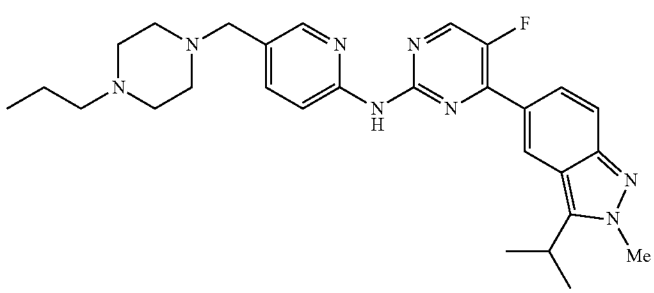 [SMILES: CCCN1CCN(Cc2ccc(Nc3ncc(F)c(-c4ccc5nn(C)c(C(C)C)c5c4)n3)nc2)CC1] | 5-fluoro-4-(3-isopropyl-2-methyl-2H-indazol-5-yl)-N-(5-((4-propylpiperazin-1-yl)methyl)pyridin-2-yl)pyrimidin-2-amine |

| Compound No. | Structure | Name |
|---|---|---|
| 16 | 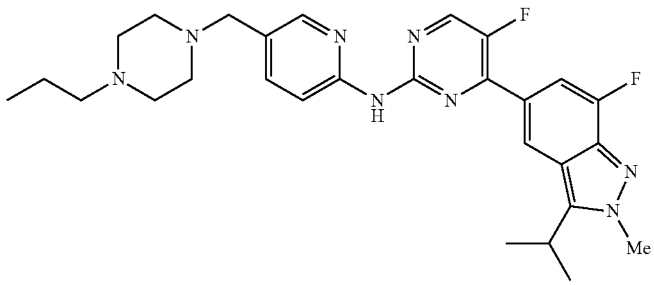 [SMILES: CCCN1CCN(Cc2ccc(Nc3ncc(F)c(-c4cc(F)c5nn(C)c(C(C)C)c5c4)n3)nc2)CC1] | 5-fluoro-4-(7-fluoro-3-isopropyl-2-methyl-2H-indazol-5-yl)-N-(5-((4-propylpiperazin-1-yl)methyl)pyridin-2-yl)pyrimidin-2-amine |
| 17 | 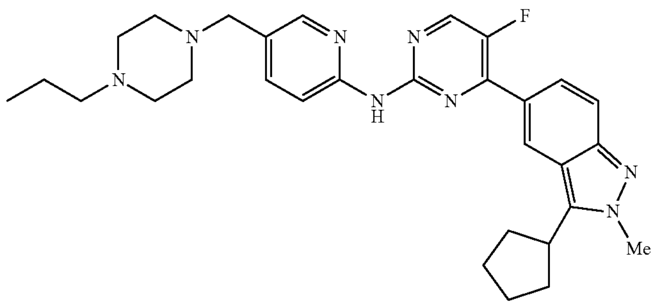 [SMILES: CCCN1CCN(Cc2ccc(Nc3ncc(F)c(-c4ccc5nn(C)c(C6CCCC6)c5c4)n3)nc2)CC1] | 4-(3-cyclopentyl-2-methyl-2H-indazol-5-yl)-5-fluoro-N-(5-((4-propylpiperazin-1-yl)methyl)pyridin-2-yl)pyrimidin-2-amine |
| 18 | 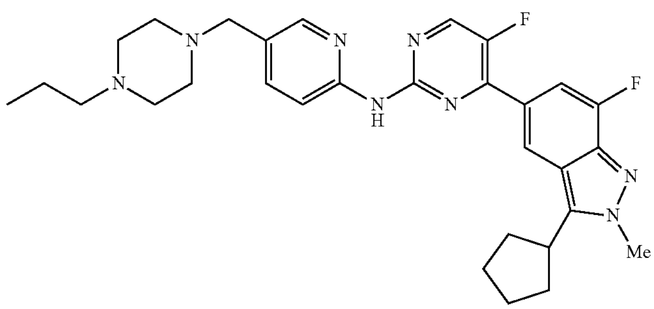 [SMILES: CCCN1CCN(Cc2ccc(Nc3ncc(F)c(-c4cc(F)c5nn(C)c(C6CCCC6)c5c4)n3)nc2)CC1] | 4-(3-cyclopentyl-7-fluoro-2-methyl-2H-indazol-5-yl)-5-fluoro-N-(5-((4-propylpiperazin-1-yl)methyl)pyridin-2-yl)pyrimidin-2-amine |
| 19 | 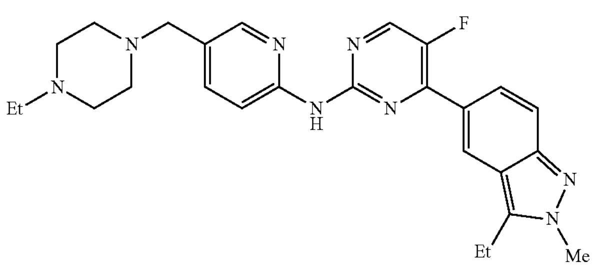 [SMILES: CCc1c2cc(-c3nc(Nc4ccc(CN5CCN(CC)CC5)cn4)ncc3F)ccc2nn1C] | 4-(3-ethyl-2-methyl-2H-indazol-5-yl)-N-(5-((4-ethylpiperazin-1-yl)methyl)pyridin-2-yl)-5-fluoropyrimidin-2-amine |
| 20 | 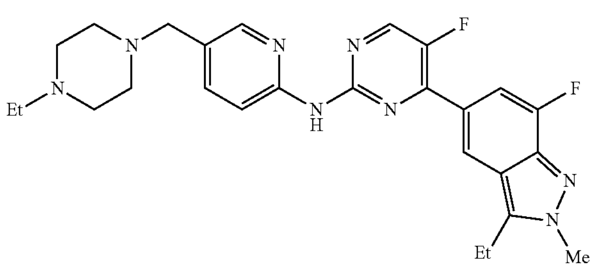 [SMILES: CCc1c2cc(-c3nc(Nc4ccc(CN5CCN(CC)CC5)cn4)ncc3F)cc(F)c2nn1C] | 4-(3-ethyl-7-fluoro-2-methyl-2H-indazol-5-yl)-N-(5-((4-ethylpiperazin-1-yl)methyl)pyridin-2-yl)-5-fluoropyrimidin-2-amine |

-continued

| Compound No. | Structure | Name |
|---|---|---|
| 21 | 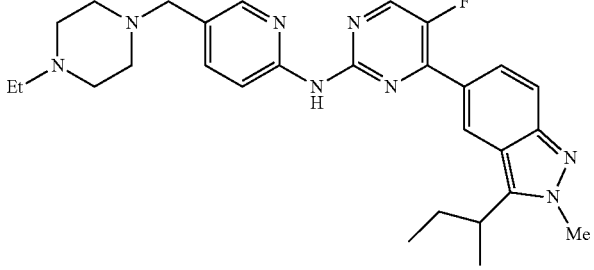 | 4-(3-(sec-butyl)-2-methyl-2H-indazol-5-yl)-N-(5-((4-ethylpiperazin-1-yl)methyl)pyridin-2-yl)-5-fluoropyrimidin-2-amine |
| 22 | 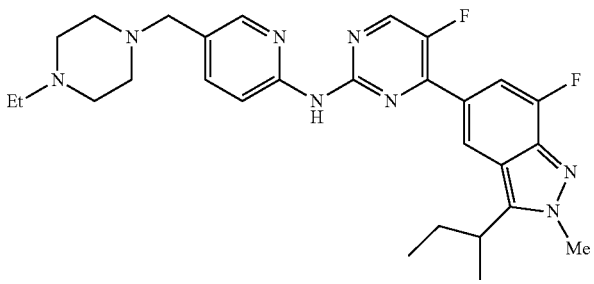 [SMILES: CCC(C)c1c2cc(-c3nc(Nc4ccc(CN5CCN(CC)CC5)cn4)ncc3F)cc(F)c2nn1C] | 4-(3-(sec-butyl)-7-fluoro-2-methyl-2H-indazol-5-yl)-N-(5-((4-ethylpiperazin-1-yl)methyl)pyridin-2-yl)-5-fluoropyrimidin-2-amine |
| 23 | 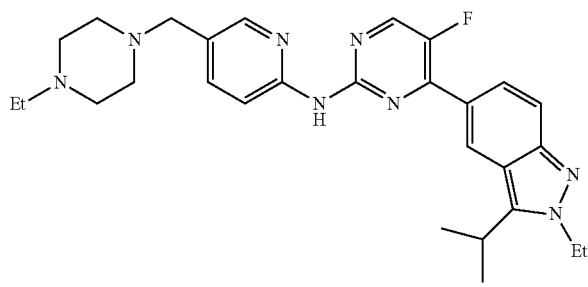 [SMILES: CCN1CCN(Cc2ccc(Nc3ncc(F)c(-c4ccc5nn(CC)c(C(C)C)c5c4)n3)nc2)CC1] | 4-(2-ethyl-3-isopropyl-2H-indazol-5-yl)-N-(5-((4-ethylpiperazin-1-yl)methyl)pyridin-2-yl)-5-fluoropyrimidin-2-amine |
| 24 | 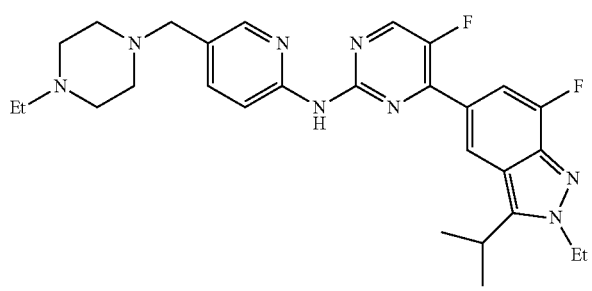 [SMILES: CCN1CCN(Cc2ccc(Nc3ncc(F)c(-c4cc(F)c5nn(CC)c(C(C)C)c5c4)n3)nc2)CC1] | 4-(2-ethyl-7-fluoro-3-isopropyl-2H-indazol-5-yl)-N-(5-((4-ethylpiperazin-1-yl)methyl)pyridin-2-yl)-5-fluoropyrimidin-2-amine |
| 25 | 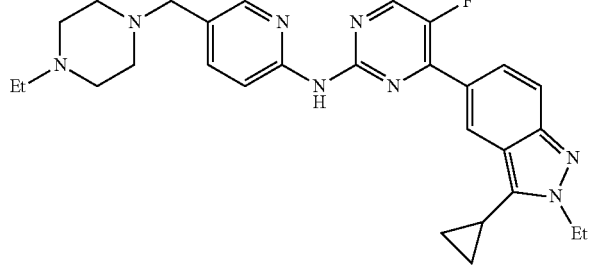 | 4-(3-cyclopropyl-2-ethyl-2H-indazol-5-yl)-N-(5-((4-ethylpiperazin-1-yl)methyl)pyridin-2-yl)-5-fluoropyrimidin-2-amine |

-continued

| Compound No. | Structure | Name |
|---|---|---|
| 26 | 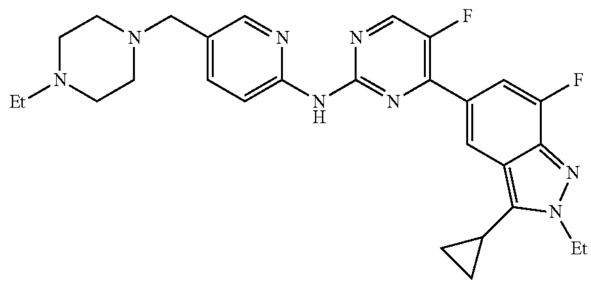 [SMILES: CCN1CCN(Cc2ccc(Nc3ncc(F)c(-c4cc(F)c5nn(CC)c(C6CC6)c5c4)n3)nc2)CC1] | 4-(3-cyclopropyl-2-ethyl-7-fluoro-2H-indazol-5-yl)-N-(5-((4-ethylpiperazin-1-yl)methyl)pyridin-2-yl)-5-fluoropyrimidin-2-amine |
| 27 | 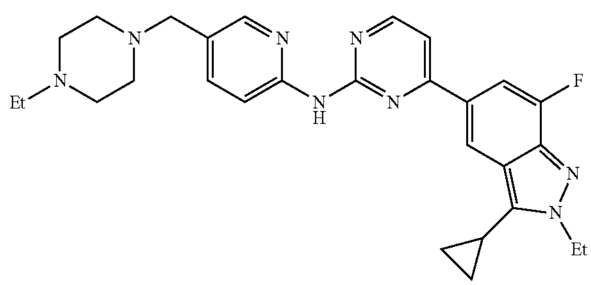 [SMILES: CCN1CCN(Cc2ccc(Nc3nccc(-c4cc(F)c5nn(CC)c(C6CC6)c5c4)n3)nc2)CC1] | 4-(3-(cyclopropylmethyl)-2-methyl-2H-indazol-5-yl)-N-(5-((4-ethylpiperazin-1-yl)methyl)pyridin-2-yl)-5-fluoropyrimidin-2-amine |
| 28 | 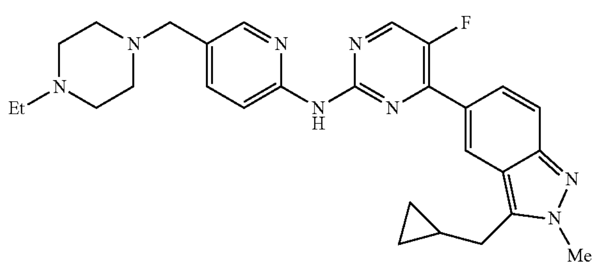 [SMILES: CCN1CCN(Cc2ccc(Nc3ncc(F)c(-c4ccc5nn(C)c(CC6CC6)c5c4)n3)nc2)CC1] | 4-(3-(cyclopropylmethyl)-7-fluoro-2-methyl-2H-indazol-5-yl)-N-(5-((4-ethylpiperazin-1-yl)methyl)pyridin-2-yl)-5-fluoropyrimidin-2-amine |
| 29 | 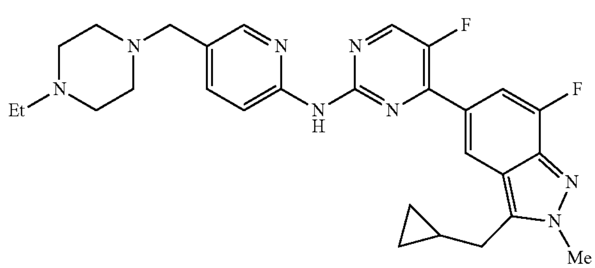 [SMILES: CCN1CCN(Cc2ccc(Nc3ncc(F)c(-c4cc(F)c5nn(C)c(CC6CC6)c5c4)n3)nc2)CC1] | 4-(3-cyclopropyl-2-ethyl-7-fluoro-2H-indazol-5-yl)-N-(5-((4-ethylpiperazin-1-yl)methyl)pyridin-2-yl)pyrimidin-2-amine |
| 30 | 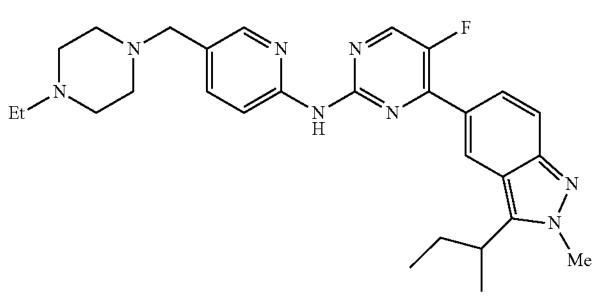 [SMILES: CCC(C)c1c2cc(-c3nc(Nc4ccc(CN5CCN(CC)CC5)cn4)ncc3F)ccc2nn1C] | 4-(3-(sec-butyl)-2-methyl-2H-indazol-5-yl)-N-(5-((4-ethylpiperazin-1-yl)methyl)pyridin-2-yl)-5-fluoropyrimidin-2-amine |

-continued

| Compound No. | Structure | Name |
|---|---|---|
| 31 | 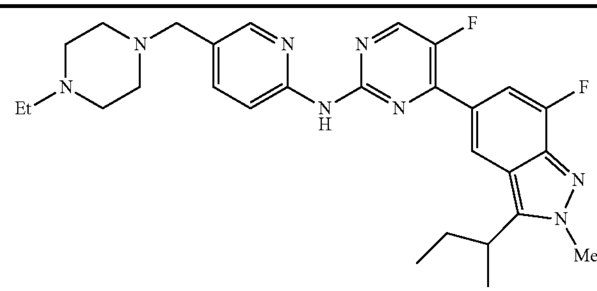 | 4-(3-(sec-butyl)-7-fluoro-2-methyl-2H-indazol-5-yl)-N-(5-((4-ethylpiperazin-1-yl)methyl)pyridin-2-yl)-5-fluoropyrimidin-2-amine |

14. A pharmaceutical composition comprising a compound of claim 1, or a pharmaceutically acceptable salt, solvate, or prodrug thereof, and one or more pharmaceutically acceptable adjuvants, diluents, and/or carriers.

15. A method of relieving, ameliorating, or modulating a disease, disorder, or condition mediated through activity of at least one cyclin-dependent kinase (CDK), comprising administering to a subject in need thereof a therapeutically effective amount of the compound of claim 1, or a pharmaceutically acceptable salt, solvate, or prodrug thereof.

16. The method of claim 15, wherein said at least one CDK is CDK4, CDK6, or a combination thereof.

17. The method of claim 15, wherein said disease or disorder is cancer.

18. The method of claim 17, wherein said cancer is selected from the group consisting of colorectal cancer, breast cancer, lung cancer, especially non-small cell lung cancer (NSCLC), prostate cancer, glioblastoma, mantel cell lymphoma (MCL), chronic myeloid leukemia (CML), and acute myeloid leukemia (AML), and complications thereof.

19. The method of claim 15, wherein said disease or disorder is an inflammation-related disease or condition selected from arthritis and cystic fibrosis.

20. The method of claim 15, in combination with administering to said subject a second therapeutic agent.

21. The method of claim 20, wherein said second therapeutic agent is a different CDK inhibitor, HER2 inhibitor, mTOR inhibitor, or EGFR inhibitor.

22. A method of inhibiting cell proliferation comprising treating proliferative cells with an effective amount of a compound claim 1, or a salt, solvate, or prodrug thereof.

23. A method of inhibiting a cyclin-dependent kinase (CDK) comprising treating said kinase with an effective amount of a compound of claim 1, or a salt, solvate, prodrug, or composition thereof.

24. The method of claim 23, wherein said cyclin-dependent kinase is CDK4, CDK6, or a combination thereof.

25. A method of relieving, ameliorating, or modulating a disease, disorder, or condition mediated through activity of at least one cyclin-dependent kinase (CDK), comprising administering to a subject in need thereof a therapeutically effective amount of a pharmaceutical composition of claim 14.

26. The method of claim 25, wherein said CDK is CDK4, CDK6, or a combination thereof.

27. The method of claim 25, wherein said disease or disorder is selected from the group consisting of colorectal cancer, breast cancer, lung cancer, especially non-small cell lung cancer (NSCLC), prostate cancer, glioblastoma, mantel cell lymphoma (MCL), chronic myeloid leukemia (CML), acute myeloid leukemia (AML), and inflammation-related diseases and conditions.

28. A method of preparing a compound of formula (I), comprising a step of coupling intermediate E with intermediate G:

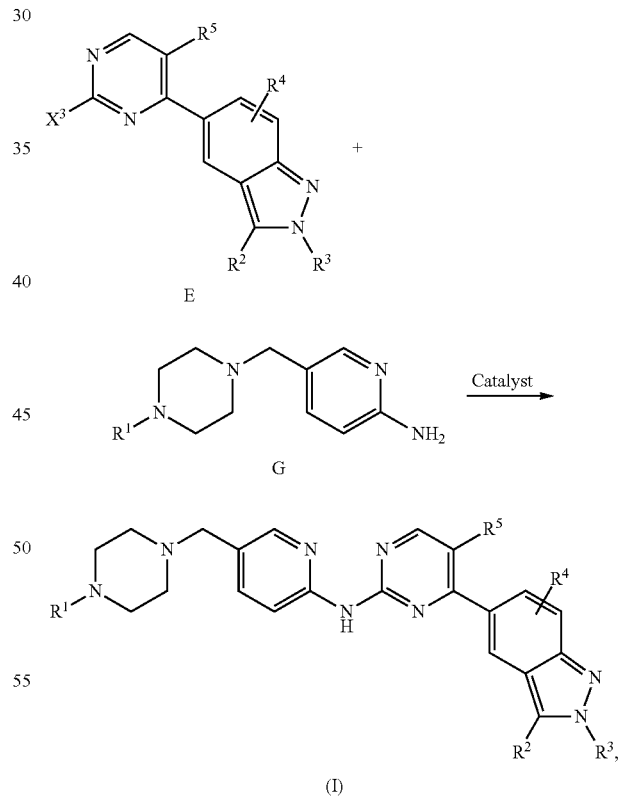

wherein $R^1$ through $R^5$ are defined as in claim 1, and $X^3$ is Cl, Br, or I.

29. The method of claim 28, further comprising the steps of converting intermediate C to intermediate D and coupling the intermediate D with a pyrimidine compound H to form the intermediate E:

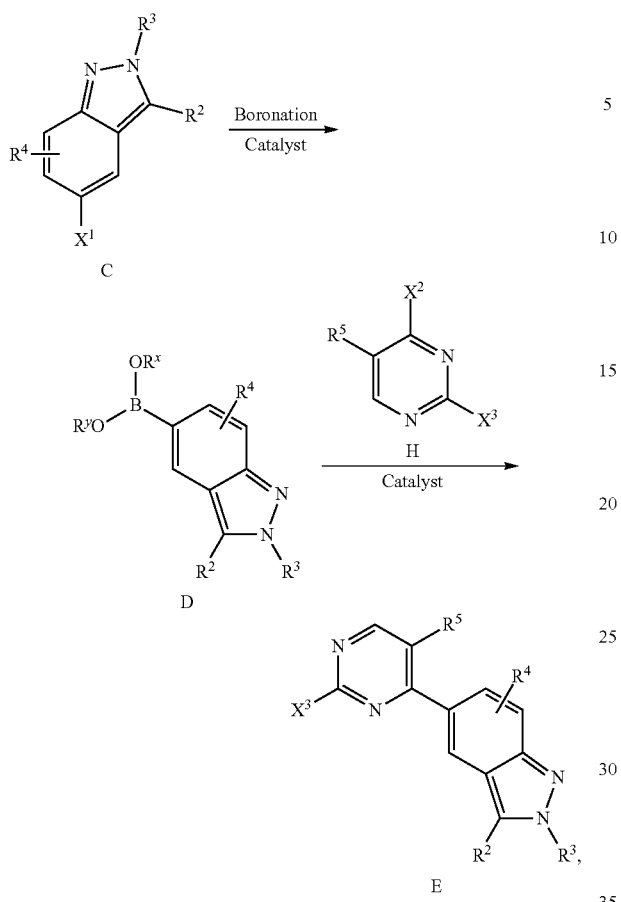

wherein $R^x$ and $R^y$ are independent alkyl, aryl, cycloalkyl, or alternatively together form an alkylene group, each optionally substituted by one or more substituents independently selected from $C_1$-$C_4$ alkyl, halogen and phenyl; and wherein $X^1$, $X^2$, and $X^3$ are each independently Cl, Br, or I, on condition that the intermediate D couples with the compound H selectively at the $X^2$ site over the $X^3$ site.

30. The method of claim 28, further comprising the steps of converting starting material S1 to intermediate A and converting the intermediate A to the intermediate C:

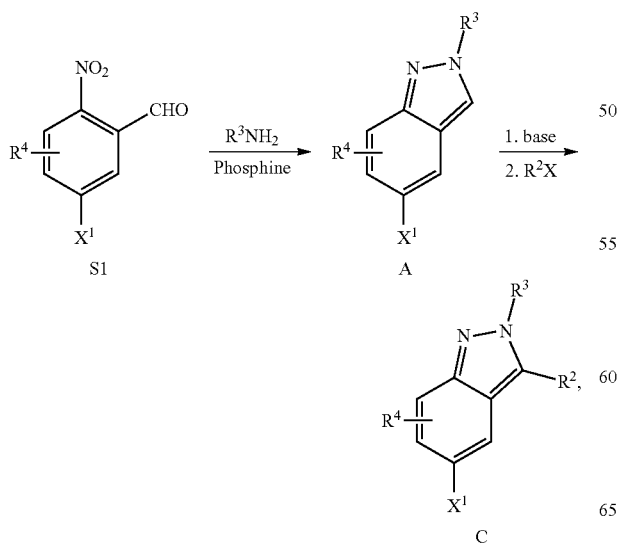

wherein X is Cl, Br, I, or $MeSO_3$—; and $R^2$ and $R^3$ are defined as in claim 28.

31. The method of claim 30, wherein said converting the intermediate A to the intermediate C, alternatively, comprises converting the intermediate A to an alcohol intermediate B followed by reduction of the alcohol intermediate B to form the intermediate C:

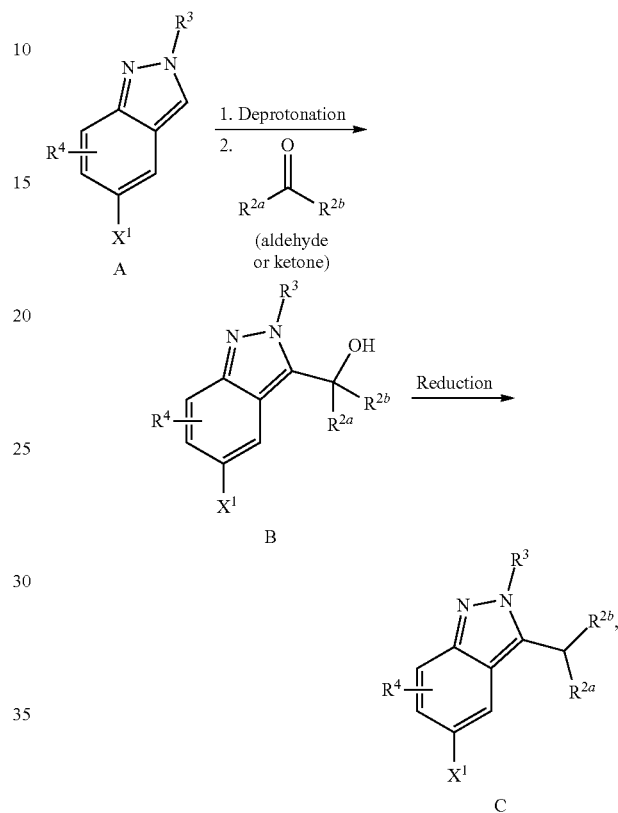

wherein $R^{2a}$ and $R^{2b}$ are each independently hydrogen, alkyl, cycloalkyl, or together form an alkylene group so that the group

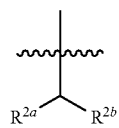

formed in the intermediate C is $R^2$ as defined in claim 30.

32. The method of claim 28, further comprising a step of forming the intermediate G through coupling the pyridine aldehyde compound S2 and the piperazine compound S3 to form an intermediate F, followed by converting the intermediate F to the intermediate G:

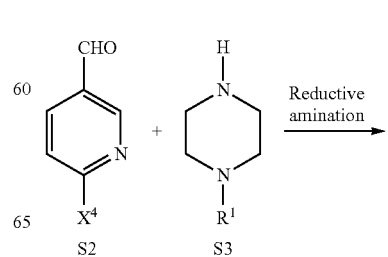

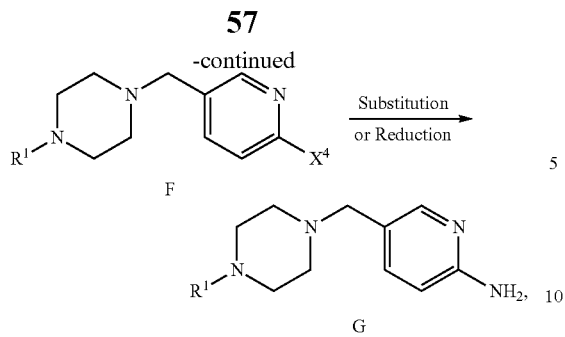
wherein $X^4$ is selected from the group consisting of Cl, Br, I, and —$NO_2$; and
wherein said converting the intermediate F to the intermediate G comprises replacing —$X^4$ with —$NH_2$ when $X^4$ is Cl, Br, or I; or reducing the nitro group (—$NO_2$) to amino group (—$NH_2$) when $X^4$ is $NO_2$.
* * * * *

UNITED STATES PATENT AND TRADEMARK OFFICE
CERTIFICATE OF CORRECTION

Page 1 of 3

PATENT NO. : 9,878,994 B2
APPLICATION NO. : 15/328813
DATED : January 30, 2018
INVENTOR(S) : Michael Nicholas Greco et al.

It is certified that error appears in the above-identified patent and that said Letters Patent is hereby corrected as shown below:

In the Specification

In Column 2, formula I, that portion of the formula appearing as:

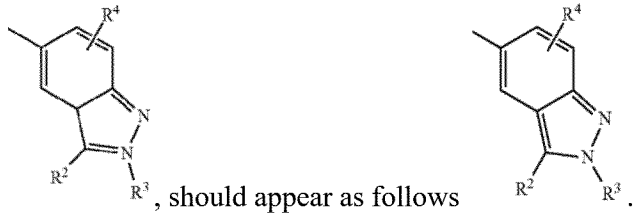

In Column 3, Lines 34-45, formula (I), that portion of the formula appearing as:

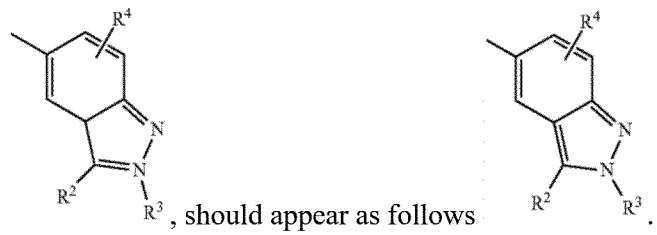

In Column 4, Lines 10-21, formula (Ia), that portion of the formula appearing as:

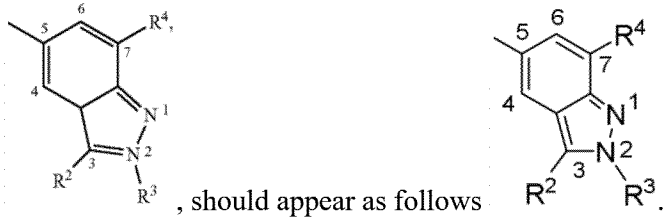

Signed and Sealed this
Thirteenth Day of April, 2021

Drew Hirshfeld
*Performing the Functions and Duties of the
Under Secretary of Commerce for Intellectual Property and
Director of the United States Patent and Trademark Office*

In Column 5, Lines 1-13, formula (Ic), that portion of the formula appearing as:
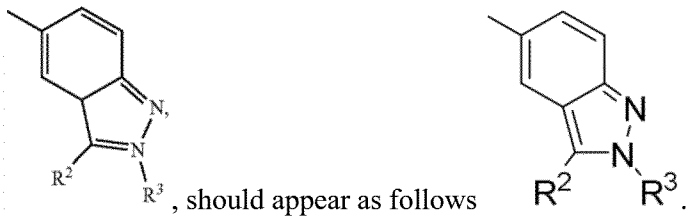
In Column 5, Lines 15-22, formula (Id), that portion of the formula appearing as:
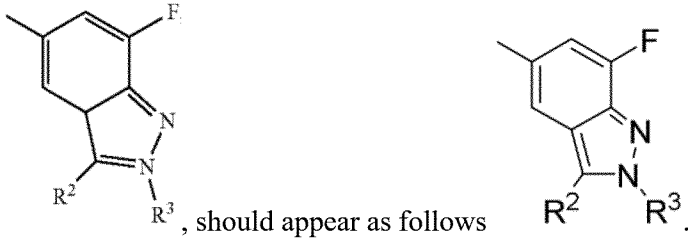
In Column 5, Lines 23-34, formula (Ie), that portion of the formula appearing as:
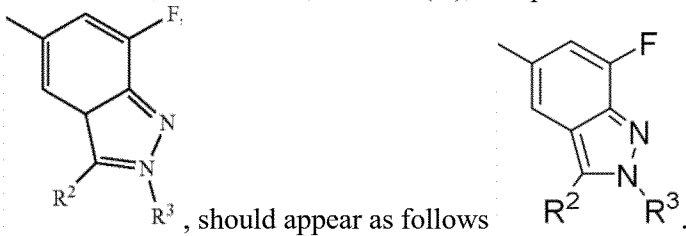
In Column 11, Lines 31-42, formula II, that portion of the formula appearing as:
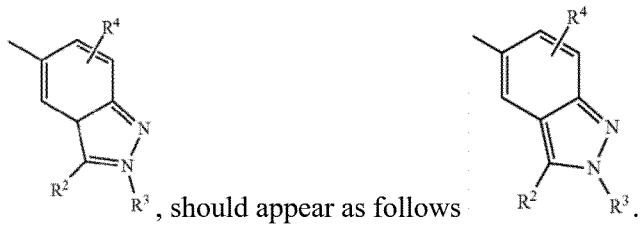
In the Claims
In Claim 1, formula (I), that portion of the formula appearing as:
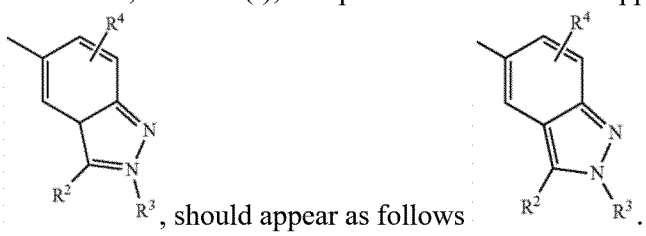

In Claim 8, formula (Ia), that portion of the formula appearing as:
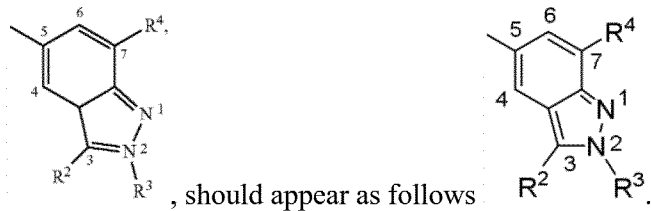 , should appear as follows 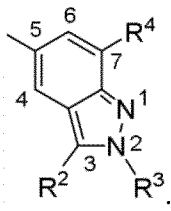 .
In Claim 12, formula (Ic), that portion of the formula appearing as:
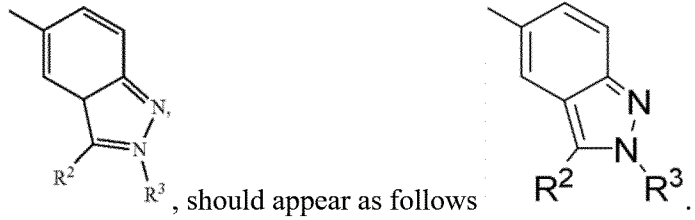 , should appear as follows 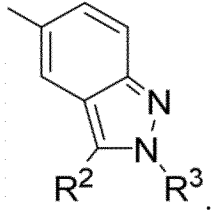 .
In Claim 12, formula (Id), that portion of the formula appearing as:
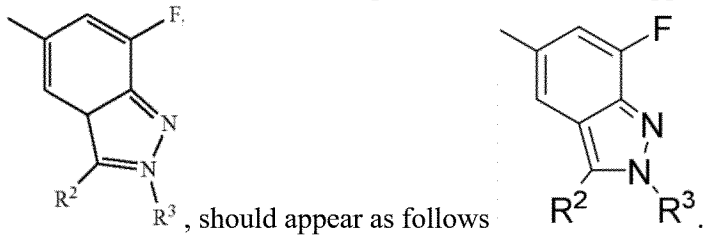 , should appear as follows 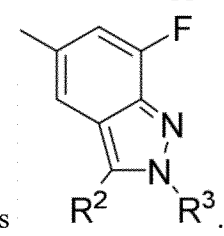 .
In Claim 12, formula (Ie), that portion of the formula appearing as:
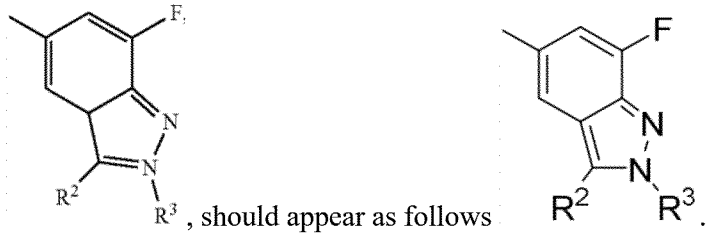 , should appear as follows 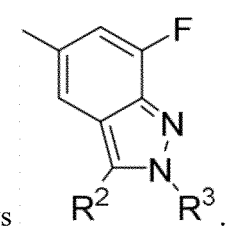 .